(12) United States Patent
Renslo et al.

(10) Patent No.: US 8,618,096 B2
(45) Date of Patent: Dec. 31, 2013

(54) PRODRUG COMPOSITIONS AND METHODS FOR USING THE SAME IN TREATING CANCER AND MALARIA

(75) Inventors: Adam Renslo, Oakland, CA (US); Sumit Mahajan, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 1 day.

(21) Appl. No.: 13/055,124

(22) PCT Filed: Jul. 21, 2009

(86) PCT No.: PCT/US2009/051304
§ 371 (c)(1),
(2), (4) Date: Apr. 18, 2011

(87) PCT Pub. No.: WO2010/011684
PCT Pub. Date: Jan. 28, 2010

(65) Prior Publication Data
US 2011/0190291 A1    Aug. 4, 2011

Related U.S. Application Data

(60) Provisional application No. 61/082,456, filed on Jul. 21, 2008.

(51) Int. Cl.
| | |
|---|---|
| *A61K 31/4025* | (2006.01) |
| *A61K 31/357* | (2006.01) |
| *A61P 33/06* | (2006.01) |
| *C07D 413/12* | (2006.01) |
| *C07D 413/14* | (2006.01) |
| *C07D 405/12* | (2006.01) |
| *C07D 311/96* | (2006.01) |
| *C07D 323/02* | (2006.01) |

(52) U.S. Cl.
USPC ............. 514/234.2; 514/232.8; 514/235.2; 514/233.5; 514/409; 514/462; 544/70; 544/148; 549/333; 549/339; 549/342; 549/431

(58) Field of Classification Search
USPC ......................................................... 549/352
See application file for complete search history.

(56) References Cited

U.S. PATENT DOCUMENTS

| | | | |
|---|---|---|---|
| 4,631,190 | A | 12/1986 | Shen et al. |
| 4,861,760 | A | 8/1989 | Mazuel et al. |
| 4,911,920 | A | 3/1990 | Jani et al. |
| 4,997,913 | A | 3/1991 | Hellstrom et al. |
| 5,140,013 | A | 8/1992 | Gaudreault et al. |
| 5,212,162 | A | 5/1993 | Missel et al. |
| 5,306,809 | A | 4/1994 | Boon et al. |
| 5,403,841 | A | 4/1995 | Lang et al. |
| 5,578,637 | A | 11/1996 | Lai et al. |
| 2008/0125441 | A1 * | 5/2008 | Vennerstrom et al. ... 514/254.11 |

FOREIGN PATENT DOCUMENTS

| | | |
|---|---|---|
| JP | 2005-112799 A1 | 4/2005 |
| JP | 2005112799 A * | 4/2005 |
| WO | WO/03/000676 A1 | 1/2003 |
| WO | WO/2005/110396 A2 | 11/2005 |

OTHER PUBLICATIONS

Abdel-Magid, Ahmed F. et al., "Reductive Amination of Aldehydes and Ketones with Sodium Triacetoxyborohydride. Studies on Direct and Indirect Reductive Amination Procedures[1]", Journal of Organic Chemistry 61:3849-3862, Jan. 1996.
Adam, Waldemar et al., "Titanium-Catalyzed Diastereoselective Epoxidations of Ene Diols and Allylic Alcohols with β-Hydroperoxy Alcohols as Novel Oxygen Donors", Journal of Organic Chemistry 62:3183-3189, Jan. 1997.
Arbuj, Sudhir S. et al., "Photochemical a-bromination of ketones using N-bromosuccinimide: a simple, mild and efficient method", Tetrahedron Letters 48:1411-1415, 2007.
Boeckman, R. J., "1,1,1-Triacetoxy-1,1-dihydro-1,2-benziodoxol-3(1H)-onel" In*Encyclopedia of Reagents for Organic Synthesis*: L.A. Paquette, Ed; Wiley: Chichester, UK, 1995, 7:4982-4987.
Boswell, G., "Synthesis and Anti-tetrabenazine Activity of C-3 Analogues of Dimethyl-2-phenlymorpholines", Journal of Heterocyclic Chemistry 33(1):33-39, 1996.
Carabateas Philip M. et al., "1-Ethyl-1, 4-dihydro-oxo-7-(pyridinyl)-3-quinolinecarboxylic Acids. I. Synthesis of 3- and 4-(3-Aminophenyl)pyridine Intermediates", Journal of Heterocyclic Chemistry 21:1849-1856, 1984.
Creek, Darren J. et al., "Iron-Mediated Degradation Kinetics of Substituted Dispiro-1,2,4-trioxolane Antimalarials", Journal of Pharmaceutical Sciences 96(11):2945-2956, Nov. 2007.
De Kimpe, Norbert et al., "Regiospecific Synthesis of α-Ketoacetals by Rearrangement of α-Bromo-α-Fluoroketones", Tetrahedron Letters 21:2257-2260, 1980.
Disbrow, Gary L. et al., "Dihydroartemisinin Is Cytotoxic to Papillomavirus-Expressing Epithelial Cells In vitro and In vivo", Cancer Research 65:10854-10861, Dec. 2005.
Dong, Yuxiang et al., "Dispiro-1,2,4,5-tetraoxanes via Ozonolysis of Cycloalkanone O-Methyl Oximes: A Comparison with the Peroxidation of Cycloalkanones in Acetonitrile-Sulfuric Acid Media", Journal of Organic Chemistry 63:8582-8585, 1988.
Efferth, Thomas et al., "Enhancement of Cytotoxicity of Artemisinins toward Cancer Cells by Ferrous Iron", Free Radical Biology & Medicine 37(7):998-1009, 2004.
Efferth, Thomas, "Mechanistic perspectives for 1,2,4-trioxanes in anti-cancer therapy", Drug Resistance Updates 8:85-97, 2005.
Farmer, Luc J. et al., "Retinoic Acid Receptor Ligands Based on the 6-Cyclopropyl-2,4-hexadienoic Acid", Bioorganic & Medicinal Chemistry Letters 13:261-264, 2003.
Gauthier, Jacques Y. et al., "The discovery of odanacatib (MK-0822), a selective inhibitor of cathepsin K", Bioorganic & Medicinal Chemistry Letters 18:923-928, 2008.
Grierson, D. et al., "Polonovski- and Pummerer-type Reactions and the Nef Reaction", Comprehensive Organic Synthesis 6: 924-937, 1991.
Griesbaum, Karl et al., "Diozonides from Coozonolyses of Suitable O-Methyl Oximes and Ketones", Tetrahedron 53(15): 5463-5470, 1997.

(Continued)

*Primary Examiner* — Samantha Shterengarts
*Assistant Examiner* — Amanda L Aguirre
(74) *Attorney, Agent, or Firm* — Kilpatrick Townsend & Stockton LLP

(57) ABSTRACT

Methods and compositions for treating disease caused by increased iron levels are disclosed Fluoregenic compounds and methods of using the same are also described.

18 Claims, 2 Drawing Sheets

(56) References Cited

OTHER PUBLICATIONS

Huttunen, Kristiina M. et al., "Novel Cyclic Phosphate Prodrug Approach for Cytochrome P450-activated Drugs Containing and Alcohol Functionality", Pharmaceutical Research 24:679-687, 2007.
International Preliminary Report on Patentability and Written Opinion dated Jan. 25, 2011 for International Application No. PCT/US2009/051304, 6 pages.
International Search Report dated Feb. 23, 2010 for International Application No. PCT/US2009/051304, 4 pages.
Kerr, Bernadette et al., "Dispiro-1,2,4-Trioxanes as Precursors of Medium Ring Lactones: Thermolysis of Indan-2-spiro-3'-( 1 ',2'4'-trioxane)-6'-spiro- 1 "-cyclohexane", Journal of the Chemical Society, Chemical Communications 590-593, 1985.
Krow, Grant R., "The Baeyer-Villiger Reactin", Comprehensive Organic Synthesis 7:671-688, 1991.
Kuroda, Chiaki et al., "Intramolecular Cyclization of Allylsilanes in the Synthesis of Guaian-8,12-olide. Stereoselective Formation of *trans*- and *cis*-Fused Methylenelactones", Journal of the Chemical Society, Perkin Transactions[1], 5:521-526, 1994.
Madrid, Peter B. et al., "Incorporation of an Intramolecular Hydrogen-bonding Motif in the Side-Chain of 4-Aminoquinolines Enhances Activity against Drug-Resistant *P. falciparum*", J Med Chem. 49(15):4535-4543, 2006.
O'Neill, Paul M. et al., "Application of Thiol-Olefin Co-oxygenation Methodology to a New Synthesis of the 1,2,4-Trioxane Pharmacophore", Organic Letters 6(18):3035-3038, 2004.
O'Neill, Paul M. et al., "Design and Synthesis of Endoperoxide Antimalarial Prodrug Models", Angewandte Chemie, International Edition 43:4193-4197, 2004.
Robert, Anne et al., "The key role of heme to trigger the antimalarial activity of trixanes", Coordination Chemistry Reviews 249:1927-1936, 2005.
Rosenthal, Philip J. et al., "A Malarial Cysteine Proteinase Is Necessary for Hemoglobin Degradation by *Plasmodium falciparum*", Journal of Clinical Investigation 82:1560-1566, 1988.
Rosenthal, Philip J., "Proteases and hemoglobin degradation", Molecular Approaches to Malaria 311-326, 2005.
Singh, Narendra P. et al., "Selective toxicity of dihydroartemisinin and holotransferrin toward human breast cancer cells", Life Sciences 70:49-56, 2001.
Somoza, John R. et al., "Crystal Structure of Human Cathepsin V", Biochemistry 39(41):12543-12551, 2000.
Stocks, Paul A. et al., "Evidence for a Common Non-Heme Chelatable-Iron-Dependent Activation Mechanism for Semisynthetic and Synthetic Endoperoxide Antimalarial Drugs", Angewandte Chemie, International Edition 46(33):6278-6283, 2007.
Subramanyam, Vinayakam et al., "Synthesis and Reactions of β-Hydroxyhydroperoxides", Journal of the Chemical Society, Chemical Communications 508-509, 1976.
Tang, Yuanquing et al., "Dispiro-1,2,4-trioxane Analogues of a Prototype Dispiro-1,2,4-trioxolane: Mechanistic Comparators for Artemisinin in the Context of Reaction Pathways with Iron(II)", Journal of Organic Chemistry 70(13):5103-5110, 2005.
Tang, Yuanquing et al., "Synthesis of Tetrasubstituted Ozonides by the Griesbaum Coozonolysis Reaction: Diastereoselectivity and Functional Group Transformations by Post-Ozonolysis Reactions", Journal of Organic Chemistry 69:6470-6473, 2004.
Tidwell, Thomas T., "Oxidation of Alcohols by Activated Dimethyl Sulfoxide and Related Reactions: An Update", Synthesis 857-870, 1990.

\* cited by examiner

PRODRUG COMPOSITIONS AND METHODS FOR USING THE SAME IN TREATING CANCER AND MALARIA

CROSS-REFERENCE TO RELATED APPLICATIONS

This application is a National Stage application of PCT Application No. PCT/US09/51304, filed Jul. 21, 2009, which claims the benefit of U.S. Provisional Appl. No. 61/082,456, filed Jul. 21, 2008, which is incorporated herein by reference in its entirety and for all purposes.

BACKGROUND OF THE INVENTION

The majority of chemotherapeutic agents used to treat cancer exhibit serious toxicity, resulting in undesired side effects for patients and reducing efficacy by limiting the doses that can be safely administered. Similarly, many of the therapeutics used to treat infectious diseases, including parasitic diseases, confer undesirable side effects. It would be preferable if such agents could be administered in a prodrug form that masked the inherent toxicity of the agent from irrelevant, non-diseased tissues, and yet released the fully active drug species at the desired site of action. Such a technology would have the potential to increase the therapeutic window of a variety of drugs, possibly allowing them to be used safely at a more efficacious dose, and with reduced incidence of undesired side-effects for the patient.

In normal cells and tissues, iron remains sequestered in forms that are non-toxic to the cell, bound to the iron carrying protein transferrin for example, or bound as heme within hemoglobin. Diseased tissues and cells, on the other hand, can contain higher than normal concentrations of iron. Many neoplastic cells for example over-express the transferrin receptor to increase their uptake of iron. Increased iron uptake has been proposed to explain the increased toxicity that iron-dependent endoperoxides like artemisinin exhibit towards cancer cell lines as compared to normal cells (Efferth, T. *Drug Resistance Updates*, 2005, 8:85-97). In one study, the expression level of the transferrin receptor was shown to correlate with the cytotoxicity of an artemisinin derivative towards HeLa cells (see for example Disbrow, G. L., et al Cancer Research, 2005, 65, 10854-10861). Artemisinin and its derivatives are believed to exert their cytotoxic effect via reaction with $Fe^{II}$ and the resulting generation of reactive oxygen and carbon centered radical species. The cytotoxicity of artemisinin derivatives towards leukemia, astrocytoma, and breast cancer cell lines can be potentiated by the addition of exogenous $Fe^{II}$ salts or transferrin (Efferth, T. et al Free Radical Biology & Medicine, 2004, 37, 998-1009; Singh, N. P. et al Life Sciences, 2001, 70, 49-56). U.S. Pat. No. 5,578,637 describes the use of an endoperoxide moiety (i.e., an artemisinin) to kill cancer cells under conditions that enhance intracellular iron concentrations. None of these prior works teach or suggest how higher than normal concentrations of iron in such cells could be exploited for selective delivery of a drug species via an iron-sensitive prodrug moiety.

The blood-scavenging parasites responsible for diseases such as malaria and schistosomiasis also possess biological compartments rich in ferrous iron. In malaria parasites, unbound heme is generated in the parasite digestive vacuole where hemoglobin is degraded by a number of proteases (See Rosenthal, P. J. in *Protease and hemoglobin degradation*. Molecular Approaches to Malaria, 2005: p. 311-326). Hence, while the concentration of unbound, ferrous iron is vanishingly small in human plasma ($\sim 10^{-16}$M), significant quantities of ferrous iron are present within malaria parasites (see Robert, A. et al Coordination Chemistry Reviews, 2005, 249, p. 1927-1936). The antimalarial drug artemisinin and its related synthetic derivatives are thought to confer their antiparasitic effect via reaction with ferrous iron and the resulting generation of reactive oxygen and carbon centered radical species. An excess of iron, and ferrous iron in particular, is therefore a distinguishing characteristic of many neoplastic cells and pathogenic parasites.

Among synthetic endoperoxide ring systems, the iron reactivity of 1,2,4-trioxolanes has been extensively studied in vitro using model systems (see Creek, D. J. et al, J. Pharm. Sci. 2007, 96, 2945-2956). As shown in FIG. 1, exposure of trioxolane A to iron(II) acetate, leads primarily to the formation of cyclohexanone (E) and the adamantane-derived lactone D, presumably via intermediates B and C (Tang, Y. et al J. Org. Chem. 2005, 70, 5103-5110). O'Neill and co-workers have devised endoperoxide systems in which the carbonyl compound formed upon reaction with iron is itself a chalcone species with antimalarial activity (O'Neill et al, Angewandte Chemie, International Edition, 2004, 43, 4193-4197 and Org. Lett. 2004, 6, 3035-3038). Although these systems can be viewed as prodrugs of chalcones, this work in no way teaches or suggests how the approach might be applied to a wide variety of drug species (i.e., drugs other than chalcones). Further, attachment of a blocking moiety ("pro" moiety) at a carbonyl function as reported in this work is much less desirable and is of less utility than attachment at an amine or alcohol function.

The use of prodrugs to confer improved properties such as increased bioavailability or aqueous solubility is a well established concept in the art of pharmaceutical research. These standard approaches rely on the action of serum esterases or phosphatases to remove the blocking pro moiety and thereby liberate the drug species. The attachment of a cytotoxic agent to a targeting moiety such as a protein or antibody via an acid-labile linker moiety is another known prodrug approach, intended to deliver a drug moiety to a specific cell or tissue. See U.S. Pat. No. 5,306,809. Acid labile linker moieties have also been used to attach drug species to biopolymers or antibodies where the intention is that the lower pH of the diseased tissue serves to trigger release of the drug moiety. See U.S. Pat. Nos. 4,631,190; 4,997,913; 5,140,013. The use of a masked retro-Michael linker has been employed in a targeted prodrug system involving biochemical oxidation as the trigger for drug release (Huttunen, et al, 2007, *Pharm. Res.*, 24:679-687). In this system, oxidation of a cyclic phosphate prodrug by CYP-450 enzymes exposes a retro-Michael substrate that undergoes spontaneous β-elimination to release phosphorylated drug species. None of these prior studies teach or suggest how one might mask the carbonyl function of a retro-Michael substrate as a trioxane or trioxolane ring, and attach such moiety to a drug species, thereby producing a prodrug that effectively releases active drug only in cells or tissues having ferrous iron concentrations above the physiological norm.

BRIEF SUMMARY OF THE INVENTION

The present invention provides prodrug compounds and methods for the treatment of diseases that are associated with a cell or organism having increased $Fe^{II}$ levels, as well as compounds and methods for the detection of fluoregenic compounds in a cell of an organism.

In one aspect, the present invention provides a prodrug having the formula:

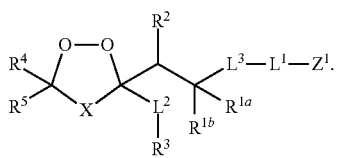

(I)

In Formula (I), X is —CH$_2$O—, —OCH$_2$—, or —O—. Z$^1$ together with L$^1$ comprise a drug moiety. L$^1$ is —N(R$^6$)—, —O— or —OC(O)—. L$^2$ is a bond, substituted or unsubstituted alkylene, substituted or unsubstituted heteroalkylene, —C(O)N(R$^7$)— or —N(R$^7$)—C(O)—. L$^3$ is —OC(O)— or a bond. If L$^1$ is —OC(O)—, then L$^3$ is a bond. R$^{1a}$ and R$^{1b}$ are independently hydrogen, substituted or unsubstituted alkyl, substituted or unsubstituted aryl, or substituted or unsubstituted heteroaryl, or R$^{1a}$ and R$^{1b}$ combine to form a substituent. R$^2$ is hydrogen or an electron withdrawing moiety. R$^3$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^4$ and R$^5$ may be joined together to form a stabilizing ring moiety having at least 6 atoms, and where that stabilizing ring moiety is selected from substituted or unsubstituted cycloalkyl, substituted or unsubstituted heterocycloalkyl, substituted or unsubstituted aryl, and substituted or unsubstituted heteroaryl. Alternatively, R$^4$ and R$^5$ are not joined together. In this alternative embodiment, R$^4$ is a stabilizing moiety having at least 6 atoms, and where that stabilizing moiety is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, and R$^5$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^6$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroary. R$^7$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In another aspect of the present invention, the prodrug compounds can be employed in methods to treat a mammalian disease that is associated with a cell or organism that has increased Fe$^{II}$ levels compared to Fe$^{II}$ levels in mammalian plasma by administering an effective amount of a prodrug compound to a patient in need of such treatment.

In another aspect, the present invention provides fluoregenic compounds having the formula:

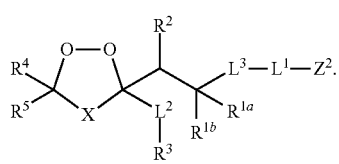

(II)

In Formula (II), X is —CH$_2$O—, —OCH$_2$—, or —O—. Z$^2$ together with L$^1$ comprise a fluoregenic moiety. L$^1$ is —N(R$^6$)— or —O—. L$^2$ is a bond, substituted or unsubstituted alkylene, substituted or unsubstituted heteroalkylene, —C(O)N(R$^7$)— or —N(R$^7$)—C(O)—. L$^3$ is —OC(O)— or a bond. R$^{1a}$ and R$^{1b}$ are independently hydrogen, substituted or unsubstituted alkyl, substituted or unsubstituted aryl, or substituted or unsubstituted heteroaryl, or R$^{1a}$ and R$^{1b}$ combine to form a substituent. R$^2$ is hydrogen or an electron withdrawing moiety. R$^3$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^4$ and R$^5$ may be joined together to form a stabilizing ring moiety having at least 6 atoms, and where that stabilizing ring moiety is substituted or unsubstituted cycloalkyl, substituted or unsubstituted heterocycloalkyl, substituted or unsubstituted aryl, or substituted or unsubstituted heteroaryl. Alternatively R$^4$ is not joined with R$^5$. In this alternative embodiment, R$^4$ is a stabilizing moiety having at least 6 atoms, and where that stabilizing moiety is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, and R$^5$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^6$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^7$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In another aspect, the present invention provides a method of detecting a fluoregenic compound in a cell of an organism, by administering this fluoregenic compound to an organism, allowing the organism to metabolize the fluoregenic compound thereby producing a fluorescent compound, and detecting this fluorescent compound in a cell of a sample from this organism.

DETAILED DESCRIPTION OF THE INVENTION

Definitions

Figure 1:
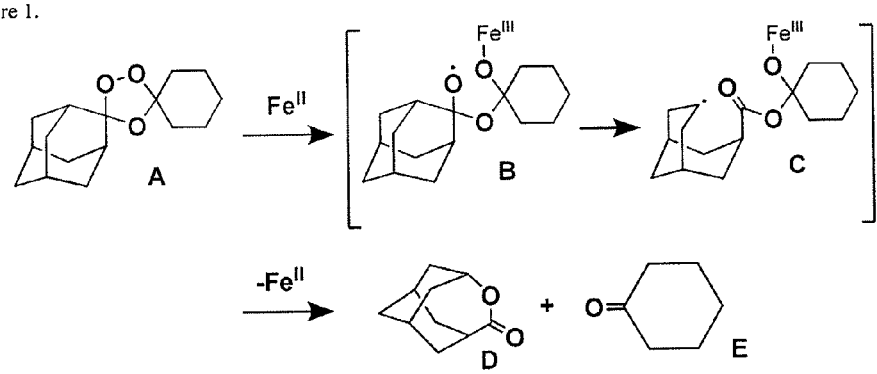
FIG. 1. Illustration of the chemical reactivity of a trioxolane containing molecule upon exposure to Fe$^{II}$. See Tang, Y. et al, *J. Org. Chem.* 2005, 70, 5103-5110).

The abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e. unbranched) or branched chain, or combination thereof, which may be fully saturated, mono- or polyunsaturated and can include di- and multivalent radicals, having the number of carbon atoms designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkyl, as exemplified, but not limited, by —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen and sulfur atoms may optionally be oxidized and the nitrogen heteroatom may optionally be quaternized. The heteroatom(s) O, N, P and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$,—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, O—CH$_3$, —O—CH$_2$—CH$_3$, and —CN. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and "heterocycloalkylene" refer to a divalent radical derived from cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. "Arylene" and "heteroarylene" refers to a divalent radical derived from a aryl and heteroaryl, respectively.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Where a heteroalkyl, heterocycloalkyl, or heteroaryl includes a specific number of members (e.g. "3 to 7 membered"), the term "member" refers to a carbon or heteroatom.

The term "oxo" as used herein means an oxygen that is double bonded to a carbon atom.

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O) NR"R"', —NR"C(O)$_2$R', —NR—C(NR'R"R"')=NR"", —NR—C(NR'R")=NR"', —S(O)R', —S(O)$_2$R', —S(O)$_2$ NR'R", —NRSO$_2$R', —CN and —NO$_2$ in a number ranging from zero to (2 m'+1), where m' is the total number of carbon atoms in such radical. R', R", R"' and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: halogen, —OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C (NR'R"R"')=NR"", —NR—C(NR'R")=NR"', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R"' and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R", R"' and R"" groups when more than one of these groups is present.

Two of the substituents on adjacent atoms of the aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"')$_d$—, where s and d are independently integers of from 0 to 3, and X' is —O—, —NR'—, —S—, —S(O)—, —S(O)$_2$—, or —S(O)$_2$NR'—. The substituents R, R', R" and R"' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

A "substituent group," as used herein, means a group selected from the following moieties:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_4$-C$_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

The compounds of the present invention may exist as salts. The present invention includes such salts. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

The term "pharmaceutically acceptable salts" is meant to include salts of the active compounds which are prepared with relatively nontoxic acids or bases, depending on the particular substituents found on the compounds described herein. The term "relatively nontoxic" refers to a level of toxicity insufficient to militate against use by a health care practitioner (for example, medical or veterinary) in the treatment of a subject. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

Thus, the compounds of the present invention may exist as salts with pharmaceutically acceptable acids. The present invention includes such salts. Examples of such salts include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Prodrugs described herein are compounds that readily undergo chemical changes under physiological conditions to provide drugs to a biological system from the drug moieties attached to the prodrug (e.g. -L$^1$-Z$^1$).

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, tautomers, geometric isomers and individual isomers are encompassed within the scope of the present invention. The compounds of the present invention do not include those which are known in the art to be too unstable to synthesize and/or isolate.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

The terms "a" or "an," as used in herein means one or more. In addition, the phrase "substituted with a[n]," as used herein, means the specified group may be substituted with one or more of any or all of the named substituents. Moreover, where a moiety is substituted with an R substituent, the group may be referred to as "R-substituted." Where a moiety is R-substituted, the moiety is substituted with at least one R substituent and each R substituent is optionally different.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods provided herein successfully treat cancer by decreasing the incidence of cancer and or causing remission of cancer.

Compositions

In one aspect, the present invention provides a prodrug having the formula:

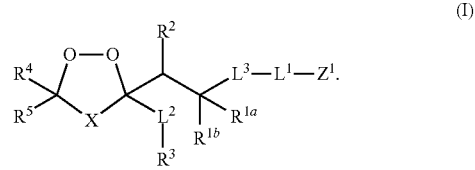

(I)

In Formula (I) X is —CH$_2$O—, —OCH$_2$—, or —O—. Z$^1$ may be a drug moiety or may form a drug moiety together with L$^1$. L$^1$ is a bond, —N(R$^6$)—, —O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. L$^2$ is a bond, substituted or unsubstituted alkylene, substituted unsubstituted heteroalkylene, substituted or unsubstituted cycloalkylene, substituted or unsubstituted heterocycloalkylene, substituted or unsubstituted arylene, substituted or unsubstituted heteroarylene, —C(O)N(R$^7$)—, or —N(R$^7$)—C(O)—. L$^3$ is —OC(O)—, substituted or unsubstituted alkylene, substituted or unsubstituted heteroalkylene or a bond, with the proviso that if L$^1$ is —OC(O)—, then L$^3$ is a bond.

R$^{1a}$ and R$^{1b}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or R$^{1a}$ and R$^{1b}$ combine to form a substituent. In some embodiments, R$^{1a}$ and R$^{1b}$ are independently hydrogen, substituted or unsubstituted alkyl, substituted or unsubstituted aryl, or substituted or unsubstituted heteroaryl, or R$^{1a}$ and R$^{1b}$ combine to form an oxo substituent. In some embodiments, R$^{1a}$ and R$^{1b}$ combine to form an oxo substituent. In other embodiments at least one of R$^{1a}$ or R$^{1b}$ is hydrogen. In other embodiments, R$^{1a}$ or R$^{1b}$ are hydrogen. In other embodiments, R$^{1a}$ is substituted or unsubstituted aryl (e.g. substituted or unsubstituted phenyl) and R$^{1b}$ is hydrogen.

R$^2$ is hydrogen, halogen, cyano, —C(O)NH$_2$, —NO$_2$, —COOH, substituted or unsubstituted alkyl, substituted or unsubstituted heteroalkyl, substituted or unsubstituted cycloalkyl, substituted or unsubstituted heterocycloalkyl, substituted or unsubstituted aryl. In some embodiments, R$^2$ includes an electron withdrawing moiety. An electron withdrawing moiety is a chemical moiety that draws electrons away from a reaction center. The electron withdrawing moiety may be monovalent or divalent. Some examples of electron withdrawing moieties include cyano (—CN), carboxamido (C(O)NH$_2$), carboxy (—C(O)—), carboxylate (—COOH), carboxyalkyl (—C(O)-alkyl), nitro (—NO$_2$), keto, and fluoro (—F).

$R^3$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^4$ and $R^5$ may be joined together to form a stabilizing ring moiety having at least 6 atoms, and where that stabilizing ring moiety is selected from substituted or unsubstituted cycloalkyl, substituted or unsubstituted heterocycloalkyl, substituted or unsubstituted aryl, and substituted or unsubstituted heteroaryl. A "stabilizing ring moiety," as used herein, refers to a ring moiety that helps to stabilize the composition provided herein to a sufficient degree to prevent premature decomposition. One of skill will understand that premature decomposition will depend on the specific use of the composition. Using the teachings provided herein along with the knowledge in the art, one of skill may select the appropriate stabilizing ring moiety to fit the specific intended use. Alternatively $R^4$ is not joined with $R^5$. In this alternative embodiment, $R^4$ is a stabilizing moiety having at least 6 atoms, and where that stabilizing moiety is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, and $R^5$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^6$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^6$ is hydrogen, substituted or unsubstituted alkyl, or substituted or unsubstituted heteroalkyl. In some embodiments, $R^6$ is hydrogen.

$R^7$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^7$ is hydrogen, substituted or unsubstituted alkyl, or substituted or unsubstituted heteroalkyl. In some embodiments, $R^7$ is hydrogen.

In some embodiments, $L^2$ is a bond, $R^8$-substituted or unsubstituted alkylene, $R^8$-substituted or unsubstituted heteroalkylene, $R^8$-substituted or unsubstituted cycloalkyl, $R^8$-substituted or unsubstituted heterocycloalkyl, $R^8$-substituted or unsubstituted aryl, $R^8$-substituted or unsubstituted heteroaryl, —C(O)N($R^7$)—, or —N($R^7$)—C(O)—.

In some embodiments, $L^1$ is —N($R^6$)—, —O—, —OC(O)—, $R^{24}$-substituted or unsubstituted alkylene, $R^{24}$-substituted or unsubstituted heteroalkylene, $R^{24}$-substituted or unsubstituted cycloalkylene, $R^{24}$-substituted or unsubstituted heterocycloalkylene, $R^{24}$-substituted or unsubstituted arylene, or $R^{24}$-substituted or unsubstituted heteroarylene.

In some embodiments, $R^{1a}$ and $R^{1b}$ may independently be hydrogen, $R^{10}$-substituted or unsubstituted alkyl, $R^{10}$-substituted or unsubstituted heteroalkyl, $R^{10}$-substituted or unsubstituted cycloalkyl, $R^{10}$-substituted or unsubstituted aryl, or $R^{10}$-substituted or unsubstituted heteroaryl, or $R^{1a}$ and $R^{1b}$ combine to form an oxo. In some embodiments, $R^{1a}$ and $R^{1b}$ are hydrogen.

In some embodiments, $R^2$ is hydrogen, halogen, cyano, —C(O)NH$_2$, —NO$_2$, —COOH, $R^{26}$-ubstituted or unsubstituted alkyl, $R^{26}$-substituted or unsubstituted heteroalkyl, $R^{26}$- substituted or unsubstituted cycloalkyl, $R^{26}$-substituted or unsubstituted heterocycloalkyl, $R^{26}$-substituted or unsubstituted aryl. In some embodiments, one of $R^{1a}$ and $R^{1b}$ is methyl or phenyl and the other is hydrogen, and $R^2$ is cyano. In some embodiments, one of $R^{1a}$ and $R^{1b}$ is phenyl and the other is hydrogen, and $R^2$ is cyano. In some embodiments, $R^{1a}$, $R^{1b}$ and $R^2$ are hydrogen.

In some embodiments, $R^3$ is $R^{12}$-substituted or unsubstituted alkyl, $R^{12}$-substituted or unsubstituted heteroalkyl, $R^{12}$-substituted or unsubstituted cycloalkyl, $R^{12}$-substituted or unsubstituted heterocycloalkyl, $R^{12}$-substituted or unsubstituted aryl, or $R^{12}$-substituted or unsubstituted heteroaryl.

In some embodiments, $R^4$ and $R^5$ may be joined together to form a stabilizing ring moiety having at least 6 atoms, and where that stabilizing ring moiety is selected from $R^{14}$-substituted or unsubstituted cycloalkyl, $R^{14}$-substituted or unsubstituted heterocycloalkyl, $R^{14}$-substituted or unsubstituted aryl, and $R^{14}$-substituted or unsubstituted heteroaryl. Alternatively, in some embodiments $R^4$ is not joined with $R^5$. In this alternative embodiment, $R^4$ is a stabilizing moiety having at least 6 atoms, and where that stabilizing moiety is selected from $R^{16}$-substituted or unsubstituted alkyl, $R^{16}$-substituted or unsubstituted heteroalkyl, $R^{16}$-substituted or unsubstituted cycloalkyl, $R^{16}$-substituted or unsubstituted heterocycloalkyl, $R^{16}$-substituted or unsubstituted aryl, and $R^{16}$-substituted or unsubstituted heteroaryl. In some embodiments, $R^5$ is hydrogen, $R^{18}$-substituted or unsubstituted alkyl, $R^{18}$-substituted or unsubstituted heteroalkyl, $R^{18}$-substituted or unsubstituted cycloalkyl, $R^{18}$-substituted or unsubstituted heterocycloalkyl, $R^{18}$-substituted or unsubstituted aryl, or $R^{18}$-substituted or unsubstituted heteroaryl.

In some embodiments, $R^6$ is hydrogen, $R^{20}$-substituted or unsubstituted alkyl, $R^{20}$-substituted or unsubstituted heteroalkyl. In some embodiments, $R^6$ is hydrogen, unsubstituted alkyl or unsubstituted heteroalkyl. In some embodiments, $R^6$ is hydrogen or unsubstituted $C_1$-$C_{10}$ alkyl. In some embodiments, $R^6$ is hydrogen.

In some embodiments, $R^7$ is hydrogen, $R^{22}$-substituted or unsubstituted alkyl, or $R^{22}$-substituted or unsubstituted heteroalkyl.

$R^8$ is independently halogen, —CN, —CF$_3$, —OH, —NH$_2$, —SO$_2$, —COOH, $R^9$-substituted or unsubstituted alkyl, $R^9$-substituted or unsubstituted heteroalkyl, $R^9$-substituted or unsubstituted cycloalkyl, $R^9$-substituted or unsubstituted heterocycloalkyl, $R^9$-substituted or unsubstituted aryl, or $R^9$-substituted or unsubstituted heteroaryl.

$R^{10}$ is independently halogen, —CN, —CF$_3$, —OH, —NH$_2$, —SO$_2$, —COOH, $R^{11}$-substituted or unsubstituted alkyl, $R^{11}$-substituted or unsubstituted heteroalkyl, $R^{11}$-substituted or unsubstituted cycloalkyl, $R^{11}$-substituted or unsubstituted heterocycloalkyl, $R^{11}$-substituted or unsubstituted aryl, or $R^{11}$-substituted or unsubstituted heteroaryl.

$R^{12}$ is independently halogen, —CN, —CF$_3$, —OH, —NH$_2$, —SO$_2$, —COOH, $R^{13}$-substituted or unsubstituted alkyl, $R^{13}$-substituted or unsubstituted heteroalkyl, $R^{13}$-substituted or unsubstituted cycloalkyl, $R^{13}$-substituted or unsubstituted heterocycloalkyl, $R^{13}$-substituted or unsubstituted aryl, or $R^{13}$-substituted or unsubstituted heteroaryl.

$R^{14}$ is independently halogen, —CN, —CF$_3$, —OH, —NH$_2$, —SO$_2$, —COOH, $R^{15}$-substituted or unsubstituted alkyl, $R^{15}$-substituted or unsubstituted heteroalkyl, $R^{15}$-substituted or unsubstituted cycloalkyl, $R^{15}$-substituted or unsubstituted heterocycloalkyl, $R^{15}$-substituted or unsubstituted aryl, or $R^{15}$-substituted or unsubstituted heteroaryl.

$R^{16}$ is independently halogen, —CN, —CF$_3$, —OH, —NH$_2$, —SO$_2$, —COOH, $R^{17}$-substituted or unsubstituted alkyl, $R^{17}$-substituted or unsubstituted heteroalkyl, $R^{17}$-substituted or unsubstituted cycloalkyl, $R^{17}$-substituted or unsubstituted heterocycloalkyl, $R^{17}$-substituted or unsubstituted aryl, or $R^{17}$-substituted or unsubstituted heteroaryl.

$R^{18}$ is independently halogen, —CN, —CF$_3$, —OH, —NH$_2$, —SO$_2$, —COOH, $R^{19}$-substituted or unsubstituted alkyl, $R^{19}$-substituted or unsubstituted heteroalkyl, $R^{19}$-substituted or unsubstituted cycloalkyl, $R^{19}$-substituted or unsubstituted heterocycloalkyl, $R^{19}$-substituted or unsubstituted aryl, or $R^{19}$-substituted or unsubstituted heteroaryl.

$R^{20}$ is independently halogen, —CN, —CF$_3$, —OH, —NH$_2$, —SO$_2$, —COOH, $R^{21}$-substituted or unsubstituted alkyl, $R^{21}$-substituted or unsubstituted heteroalkyl, $R^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl.

$R^{22}$ is independently halogen, —CN, —CF$_3$, —OH, —NH$_2$, —SO$_2$, —COOH, $R^{23}$-substituted or unsubstituted alkyl, $R^{23}$-substituted or unsubstituted heteroalkyl, $R^{23}$-substituted or unsubstituted cycloalkyl, $R^{23}$-substituted or unsubstituted heterocycloalkyl, $R^{23}$-substituted or unsubstituted aryl, or $R^{23}$-substituted or unsubstituted heteroaryl.

$R^{24}$ is independently halogen, —CN, —CF$_3$, —OH, —NH$_2$, —SO$_2$, —COOH, $R^{25}$-substituted or unsubstituted alkyl, $R^{25}$-substituted or unsubstituted heteroalkyl, $R^{25}$-substituted or unsubstituted cycloalkyl, $R^{25}$-substituted or unsubstituted heterocycloalkyl, $R^{25}$-substituted or unsubstituted aryl, or $R^{25}$-substituted or unsubstituted heteroaryl.

$R^{26}$ is independently halogen, —CN, —CF$_3$, —OH, —NH$_2$, —SO$_2$, —COOH, $R^{27}$-substituted or unsubstituted alkyl, $R^{27}$-substituted or unsubstituted heteroalkyl, $R^{27}$-substituted or unsubstituted cycloalkyl, $R^{27}$-substituted or unsubstituted heterocycloalkyl, $R^{27}$-substituted or unsubstituted aryl, or $R^{27}$-substituted or unsubstituted heteroaryl.

$R^9$, $R^{11}$, $R^{13}$, $R^{15}$, $R^{17}$, $R^{19}$, $R^{21}$, $R^{23}$, $R^{25}$, and $R^{27}$ are independently halogen, —CN, —CF$_3$, —OH, —NH$_2$, —SO$_2$, —COOH, unsubstituted alkyl, unsubstituted heteroalkyl, unsubstituted cycloalkyl, unsubstituted heterocycloalkyl, unsubstituted aryl, or unsubstituted heteroaryl.

In some embodiments, at least one or all of $R^{1a}$, $R^{1b}$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, or $R^{27}$ is a size-limited substituent or lower substituent group.

In some embodiments, the variable X in Formula (I) is —O—. In some embodiments, $R^6$ is hydrogen, unsubstituted alkyl or unsubstituted heteroalkyl. In other embodiments, $R^6$ is hydrogen or unsubstituted C$_1$-C$_{10}$ alkyl. In some embodiments, $R^6$ is hydrogen.

In some embodiments, $L^1$ is —N($R^6$)—, —O—, —OC(O)—, substituted or unsubstituted heterocycloalkylene or substituted or unsubstituted heteroarylene. In other embodiments, $L^1$ is —N($R^6$)—, —O—, —OC(O)—, or substituted or unsubstituted heterocycloalkylene. In certain embodiments, $L^1$ is —N($R^6$)—, —O—, —OC(O)—, or unsubstituted heterocycloalkylene (e.g. piperazin-diyl. $L^1$ may be —O—C(O)— and $L^3$ may be —NH— or —O—. Alternatively, $L^1$ is —NR$^6$— and $R^6$ is hydrogen. In another embodiment, $R^{1a}$ and $R^{1b}$ are hydrogen. $R^{1a}$ and/or $R^{1b}$ may also be methyl or phenyl, and $R^2$ may be cyano. In another embodiment, $R^{1a}$ is phenyl, $R^{1b}$ is hydrogen, and $R^2$ is cyano. In some embodiments, $R^{1a}$ is phenyl, $R^{1b}$ is hydrogen, and $R^2$ is hydrogen. In some embodiments, $L^3$ is —O—C(O)—, and $L^1$ is —NH— or —O—. In some embodiments, $L^1$ is —NR$^6$—, and $R^6$ is hydrogen.

In some embodiments, $L^2$ has the formula -L$^{2a}$-C(O)N(R$^7$)-L$^{2b}$ or -L$^{2a}$-C(O)N(R$^7$)-L$^{2b}$-, wherein L$^{2a}$ and L$^{2b}$ are independently a bond, substituted or unsubstituted alkylene, or substituted or unsubstituted heteroalkylene. In some embodiments, L$^{2a}$ and L$^{2b}$ are independently a bond, or substituted or unsubstituted C$_1$-C$_5$ alkylene. In some embodiments, L$^{2a}$ and L$^{2b}$ are independently a bond, or unsubstituted or substituted 2-5 membered heteroalkylene. In some embodiments, $R^7$ is hydrogen.

In other embodiments, $L^2$ has the formula —(CH$_2$)$_w$—C(O)NH—(CH$_2$)$_z$— or —(CH$_2$)$_w$—NHC(O)—(CH$_2$)$_z$—, and $R^3$ is $R^{12}$-substituted or unsubstituted heterocycloalkyl, or $R^{12}$-substituted or unsubstituted heteroaryl. The variables w and z are independently integers from 0 to 20. $R^3$ may be morpholino, and w and z are independently integers from 1 to 5.

In certain embodiments, compounds have the structure of Formula (I), wherein X is —O—, $R^{1a}$, $R^{1b}$ and $R^2$ are hydrogen, $L^2$ is N-ethylpropionamide-diyl or N-propylpropionamide-diyl, $R^3$ is morpholino or pyrrolidine-2-one-1-yl, and $L^1$, $L^3$, $R^4$, $R^5$ and $Z^1$ are as defined for Formula (I). In certain embodiments, X is —O—.

In some embodiments, $R^4$ and $R^5$ are joined together to form a $R^{14}$-substituted or unsubstituted adamantyl having the structure of Formula (III), wherein $R^{1a}$, $R^{1b}$, $R^2$, $R^3$, $R^{14}$, $L^1$, $L^2$, $L^3$ and $Z^1$ are as defined above for Formula (I), and wherein substituent $R^{14}$ is optional. In some embodiments, $R^4$ and $R^5$ are joined together to form a substituted or unsubstituted adamantyl, or substituted or unsubstituted cyclohexyl. In some embodiments, $R^4$ and $R^5$ are joined together to form a substituted or unsubstituted adamantyl.

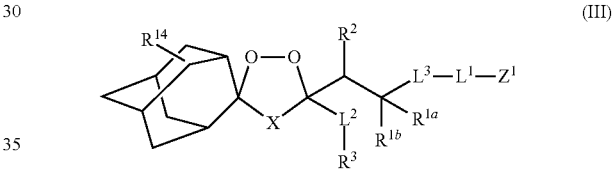

(III)

In some embodiments, $R^4$ and $R^5$ are joined together to form an $R^{14}$-substituted or unsubstituted cyclohexyl. One of skill will understand that the definitions set forth in the compounds or Formula (I) may be applied to Formula (III) in keeping with the normal rules understood in the chemical arts.

Figure 2:
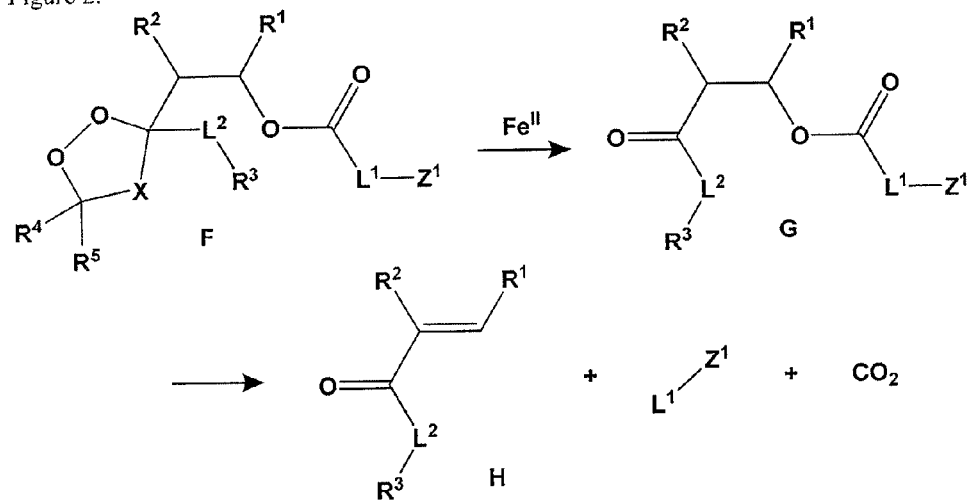
FIG. 2. Illustration of the process of prodrug activation and drug release for compounds described herein. Reaction of F with Fe$^{II}$ leads to the formation of ketone G. Beta-elimination reaction of G (with concomitant decarboxylation in cases for example where L$^3$=—OC(O)—) leads to the release of the active drug species L$^1$-Z$^1$ and ketone H.

Drug moieties that form part of the prodrugs described herein obtain functionality due to chemical changes in the prodrugs that occur under physiological conditions. As illustrated in FIG. 2, the trioxane or trioxolane ring moiety of the prodrug F may react with Fe$^{II}$, leading to the formation of ketone species G. The ketone G then undergoes a beta-elimination reaction (with concomitant decarboxylation when $L^3$ is —OC(O)—) to release the active drug moiety $L^1$-$Z^1$ and ketone H. The drug moiety obtained from the prodrug due to chemical changes under physiological conditions is capable of treating mammalian disease caused by a cell or organism having increased Fe$^{II}$ levels compared to Fe$^{II}$ levels in mammalian plasma. The mammalian disease may be a human disease. In some embodiments, the human disease may be a parasitic disease or a cancer. In yet another embodiment, the human disease may be malaria, schistosomiasis, trypanosomiasis, leukemia, cervical cancer, breast cancer, colon cancer, ovarian cancer, prostate cancer, thyroid cancer, melanoma, or any cancer where transferrin receptors (CD71) are over-expressed as compared to normal cells. In some embodiments, the drug moiety that forms part of the prodrug is chemically changed under physiological conditions to form a drug selected from amodiaquine, mefloquine, chloroquine, primaquine, imiquimod, oxamniquine, doxycycline, clindamycin, quinine, quinidine, halofantrine, artesunate, fansidar, atovaquone, pyrimethamine, proguanil, vinblastine, vincristine, daunorubicin, docetaxel, paclitaxel, irinotecan, etoposide, doxorubicin, idarubicin, mitomycin, plicamycin, topotecan, clardribine, cytarabine, fludarabine, and methotrexate. In some embodiments, the drug moiety that forms part of the prodrug is a moiety as described herein.

In some embodiments, at least one substituted or unsubstituted alkyl, heteroalkyl, cycloalkyl or heterocycloalkyl in a compound described above is a size-limited substituent group. In some embodiments, at least one of each substituted or unsubstituted alkyl, heteroalkyl, cycloalkyl or heterocycloalkyl is a lower substituent group.

In some embodiments, at least one or all substituted groups of a compound described herein is substituted with at least one substituent group. More specifically, in some embodiments, at least one or all substituted alkyl, substituted heteroalkyl, substituted cycloalkyl, substituted heterocycloalkyl, substituted aryl and substituted heteroaryl described above is substituted with at least one substituent group. In other embodiments, at least one or all such groups are substituted with at least one size-limited substituent group. Alternatively, at least one or all such groups are substituted with at least one lower substituent group.

In some embodiments, each substituted group of a compound described herein is substituted with at least one substituent group. More specifically, in some embodiments, each substituted alkyl, substituted heteroalkyl, substituted cycloalkyl, substituted heterocycloalkyl, substituted aryl and substituted heteroaryl described above is substituted with at least one substituent group. In other embodiments, at least one or all of these groups are substituted with at least one size-limited substituent group. Alternatively, at least one or all of these groups are substituted with at least one lower substituent group.

In certain embodiments, compounds have the structure of Formula (III), wherein X is —O—, $R^{1a}$, $R^{1b}$ and $R^2$ are hydrogen, $L^2$ is N-ethylpropionamide-diyl or N-propyl propionamide-diyl, $R^3$ is morpholino or pyrrolidine-2-one-1-yl, and $L^1$, $L^3$, $R^{14}$ and $Z^1$ are as defined for Formula (I).

In certain embodiments, compounds have the structure of Formula (III), wherein X is —O—, $R^{1a}$, $R^{1b}$ and $R^2$ are hydrogen, $L^2$ is N-ethylpropionamide-diyl, $R^3$ is morpholino, and $L^1$, $L^3$, $R^{14}$ and $Z^1$ are as defined for Formula (I).

In certain embodiments, compounds have the structure of Formula (III), wherein X is —O—, $R^{1a}$, $R^{1b}$ and $R^2$ are hydrogen, $L^2$ is N-propylpropionamide-diyl, $R^3$ is pyrrolidine-2-one-1-yl, and $L^1$, $L^3$, $R^{14}$ and $Z^1$ are as defined for Formula (I).

In certain embodiments, compounds have the structure of Formula (III), wherein X is —O—, one of $R^{1a}$ and $R^{1b}$ is phenyl and the other is hydrogen, $R^2$ is hydrogen, and $L^1$, $L^3$, $R^{14}$ and $Z^1$ are as defined for Formula (I).

In certain embodiments, compounds have the structure of Formula (III), wherein X is —O—, $R^{1a}$ and $R^{1b}$ are hydrogen, $R^2$ is halo, preferably fluoro, and $L^1$, $L^3$, $R^{14}$ and $Z^1$ are as defined for Formula (I).

In certain embodiments, the compound has the structure of Formula (III), wherein X is —O—, $R^{1a}$ and $R^{1b}$ together form an oxo substituent, $R^2$ is hydrogen, $L^3$ is a bond, $L^1$ is —NH—, $L^1$ and $Z^1$ together and $R^{14}$ are as defined for Formula (I). Preferably, $R^{14}$ is absent.

In certain embodiments, compounds described herein have the structure of Formula (IIIa), wherein $L^2$ is —(CH$_2$)$_w$—C(O)NH—(CH$_2$)$_z$—, w is 2, z is in the range 2-3, and $L^3$, $L^1$ and $Z^1$ are as defined for Formula (I).

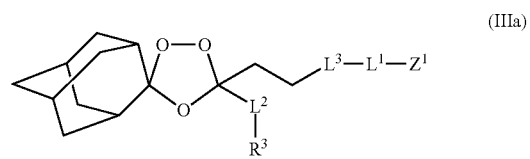

In certain embodiments, compounds described herein have the structure of Formula (IIIa), wherein $L^2$ is —(CH$_2$)$_w$—C(O)NH—(CH$_2$)$_z$—, w is 2, z is in the range 2-3, $L^3$ is a bond, and $L^1$ is —NH—.

In certain embodiments, compounds have the structure of Formula (IIIb), wherein $L^2$ is —(CH$_2$)$_w$—C(O)NH—(CH$_2$)$_z$—, w is 2, z is in the range 2-3, and $L^1$ and $Z^1$ are as defined for Formula (I). One of skill will understand that the definitions set forth in the compounds or Formula (I) may be applied to Formula (IIIa) in keeping with the normal rules understood in the chemical arts.

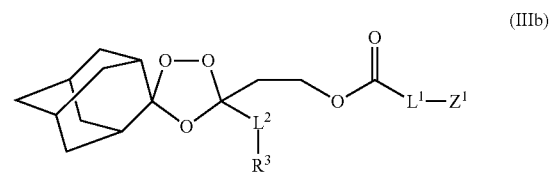

Further to embodiments relating to Formulae (III), (IIIa) or (IIIb), in certain embodiments $L^1$ is —N(R$^6$)—, and $R^6$ is hydrogen, or substituted or unsubstituted alkyl. In certain embodiments, $R^6$ is hydrogen, In certain embodiments, $R^6$ is alkyl, preferably methyl. In certain embodiments, $R^6$ is 2-furylalkyl, preferably 2-furylmethyl. In certain embodiments, $R^6$ together with a nitrogen of $Z^1$ form a piperazine. One of skill will understand that the definitions set forth in the compounds or Formula (I) may be applied to Formula (IIIb) in keeping with the normal rules understood in the chemical arts.

In certain embodiments, the compound has the structure of Formula (IIIb), wherein $L^2$ is —(CH$_2$)$_w$—C(O)NH—(CH$_2$)$_z$—, w is 2, z is in the range 2-3, $R^3$ is morpholino or pyrrolidine-2-one-1-yl, $L^1$ is —O—, and $L^1$-$Z^1$ form a drug moiety. In some embodiments, the drug moiety is the structure following, wherein the wavy line indicates the point of bonding in the compound of Formula (IIIb):

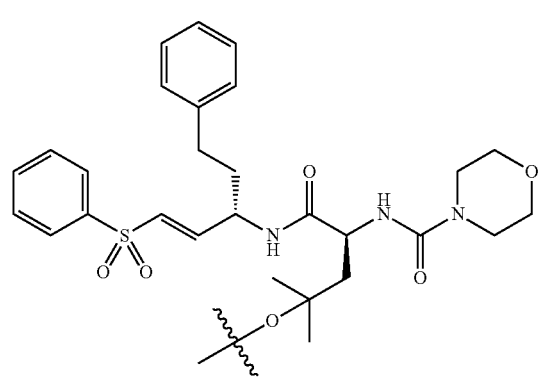 [SMILES: *OC(C)(C)C[C@H](NC(=O)N1CCOCC1)C(=O)N[C@H](/C=C/S(=O)(=O)c1ccccc1)CCc1ccccc1]

In certain embodiments, the compound has a structure as disclosed in Table 1.

In another aspect, the present invention provides fluoregenic compounds having the formula:

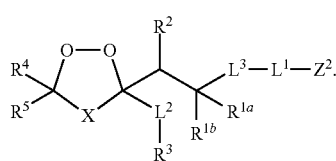

(II)

In Formula (II) X is —CH$_2$O—, —OCH$_2$—, or —O—. $Z^1$ may be a drug moiety or may form a drug moiety together with $L^1$. $L^1$ is —N($R^6$)—, —O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^2$ is a bond, substituted or unsubstituted alkylene, substituted unsubstituted heteroalkylene, substituted or unsubstituted cycloalkylene, substituted or unsubstituted heterocycloalkylene, substituted or unsubstituted arylene, substituted or unsubstituted heteroarylene, —C(O)N($R^7$)—, or —N($R^7$)—C(O)—. $L^3$ is —OC(O)—, substituted or unsubstituted alkylene, substituted or unsubstituted heteroalkylene or a bond, with the proviso that if $L^1$ is —OC(O)—, then $L^3$ is a bond.

$R^{1a}$ and $R^{1b}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or $R^{1a}$ and $R^{1b}$ combine to form a substituent. In some embodiments, $R^{1a}$ and $R^{1b}$ are independently hydrogen, substituted or unsubstituted alkyl, substituted or unsubstituted aryl, or substituted or unsubstituted heteroaryl, or $R^{1a}$ and $R^{1b}$ combine to form an oxo. In some embodiments, $R^{1a}$ and $R^{1b}$ combine to form an oxo substituent. In other embodiments at least one of $R^{1a}$ or $R^{1b}$ is hydrogen. In other embodiments, $R^{1a}$ or $R^{1b}$ are hydrogen. In other embodiments, $R^{1a}$ is substituted or unsubstituted aryl (e.g. substituted or unsubstituted phenyl) and $R^{1b}$ is hydrogen.

$R^2$ is hydrogen, halogen, cyano, —C(O)NH$_2$, —NO$_2$, —COOH, substituted or unsubstituted alkyl, substituted or unsubstituted heteroalkyl, substituted or unsubstituted cycloalkyl, substituted or unsubstituted heterocycloalkyl, substituted or unsubstituted aryl. In some embodiments, $R^2$ includes an electron withdrawing moiety as defined herein and known in the art.

$R^3$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^4$ and $R^5$ may be joined together to form a stabilizing ring moiety, as defined herein, having at least 6 atoms, and where that stabilizing ring moiety is selected from substituted or unsubstituted cycloalkyl, substituted or unsubstituted heterocycloalkyl, substituted or unsubstituted aryl, and substituted or unsubstituted heteroaryl. Alternatively $R^4$ is not joined with $R^5$. In this alternative embodiment, $R^4$ is a stabilizing moiety having at least 6 atoms, and where that stabilizing moiety is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, and $R^5$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^6$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^7$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments, in compounds having the structure of Formula (II), $L^2$ is a bond, $R^8$-substituted or unsubstituted alkylene, or $R^8$-substituted, unsubstituted heteroalkylene, —C(O)N($R^7$)—, or —N($R^7$)—C(O)—. $L^1$ is —N($R^6$)—, —O—, —OC(O)—, $R^{24}$-substituted or unsubstituted alkylene, $R^{24}$-substituted or unsubstituted heteroalkylene, $R^{24}$-substituted or unsubstituted cycloalkylene, $R^{24}$-substituted or unsubstituted heterocycloalkylene, $R^{24}$-substituted or unsubstituted arylene, or $R^{24}$-substituted or unsubstituted heteroarylene. $R^{1a}$ and $R^{1b}$ are independently hydrogen, $R^{10}$-substituted or unsubstituted alkyl, $R^{10}$-substituted or unsubstituted aryl, or $R^{10}$-substituted or unsubstituted heteroaryl, or $R^{1a}$ and $R^{1b}$ combine to form a substituent. $R^2$ is hydrogen, halogen, cyano, —C(O)NH$_2$, —NO$_2$, —COOH, $R^{26}$-substituted or unsubstituted alkyl, $R^{26}$-substituted or unsubstituted heteroalkyl, $R^{26}$-substituted or unsubstituted cycloalkyl, $R^{26}$-substituted or unsubstituted heterocycloalkyl, $R^{26}$-substituted or unsubstituted aryl. $R^3$ is $R^{12}$-substituted or unsubstituted alkyl, $R^{12}$-substituted or unsubstituted heteroalkyl, $R^{12}$-substituted or unsubstituted cycloalkyl, $R^{12}$-substituted or unsubstituted heterocycloalkyl, $R^{12}$-substituted or unsubstituted aryl, or $R^{12}$-substituted or unsubstituted heteroaryl. $R^4$ and $R^3$ may be joined together to form a stabilizing ring moiety having at least 6 atoms, and where that stabilizing ring moiety is selected from $R^{14}$-substituted or unsubstituted cycloalkyl, $R^{14}$-substituted or unsubstituted heterocycloalkyl, $R^{14}$-substituted or unsubstituted aryl, and $R^{14}$-substituted or unsubstituted heteroaryl. Alternatively, in some embodiments $R^4$ is not joined with $R^3$. In this alternative embodiment, $R^4$ is a stabilizing moiety having at least 6 atoms, and where that stabilizing moiety is selected from $R^{16}$-substituted or unsubstituted alkyl, $R^{16}$-substituted or unsubstituted heteroalkyl, $R^{16}$-substituted or unsubstituted cycloalkyl, $R^{16}$-substituted or unsubstituted heterocycloalkyl, $R^{16}$-substituted or unsubstituted aryl, and $R^{16}$-substituted or unsubstituted heteroaryl. In some embodiments, $R^5$ is hydrogen, $R^{18}$-substituted or unsubstituted alkyl, $R^{18}$-substituted or unsubstituted heteroalkyl, $R^{18}$-substituted or unsubstituted cycloalkyl, $R^{18}$-substituted or unsubstituted heterocycloalkyl, $R^{18}$-substituted or unsubstituted aryl, or $R^{18}$-substituted or unsubstituted heteroaryl. $R^6$ is hydrogen, $R^{20}$-substituted or unsubstituted alkyl, $R^{20}$-substituted or unsubstituted heteroalkyl. $R^7$ is hydrogen, $R^{22}$-substituted or unsubstituted alkyl, or $R^{22}$-substituted or unsubstituted heteroalkyl.

Further to compounds having the structure of Formula (II), substituents $R^{1a}$, $R^{1b}$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$ and $R^{27}$ are as defined above.

In some embodiments, at least one or all of $R^{1a}$, $R^{1b}$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$ or $R^{27}$ a size-limited substituent or lower substituent group.

In one embodiment, the fluoregenic moiety in Formula (II) is 4-nitrobenzo-2-oxa-1,3-diazole, 7-amino-4-methylcoumarin, 7-amino-4-trifluoromethylcoumarin, para-nitroaniline, rhodamine 110, or other similar compounds bearing an amine or hydroxyl group that, when part of a carbamate or carbonate function, has attenuated fluorescence. In an exemplary embodiment, X in Formula (II) is O. $R^6$ may be hydrogen, unsubstituted alkyl or unsubstituted heteroalkyl. Alternatively, $R^6$ is hydrogen or unsubstituted $C_1$-$C_{10}$ alkyl. In other embodiments, $R^6$ is hydrogen. $L^1$ may be —O—C(O)— and $L^3$ is —NH— or —O—. Alternatively, $L^1$ is —$NR^6$— and $R^6$ is hydrogen. In other embodiments, $R^1$ and $R^2$ are hydrogen. Alternatively, $R^1$ is methyl or phenyl and $R^2$ is cyano. In another embodiment, $R^1$ is phenyl and $R^2$ is cyano. In some embodiments, $R^1$ may be phenyl and $R^2$ may be hydrogen.

In some embodiments of Formula (II), X is —O—. In some embodiments, $R^6$ is hydrogen, substituted alkyl or unsubstituted heteroalkyl. In some embodiments, $R^6$ is hydrogen or unsubstituted $C_1$-$C_{10}$ alkyl. In some embodiments, $R^6$ is hydrogen. In some embodiments, $L^3$ is —O—C(O)—, and $L^1$ is —NH— or —O—. In some embodiments, $L^1$ is —$NR^6$—, and $R^6$ is hydrogen. In some embodiments, $R^{1a}$, $R^{1b}$ and $R^2$ are hydrogen. In some embodiments, one or $R^{1a}$ and $R^{1b}$ is methyl or phenyl, and the other is hydrogen, and $R^2$ is cyano. In some embodiments, one or $R^{1a}$ and $R^{1b}$ is phenyl, and the other is hydrogen, and $R^2$ is cyano. In some embodiments, one or $R^{1a}$ and $R^{1b}$ is phenyl, and the other is hydrogen, and $R^2$ is hydrogen.

In some embodiments, $L^2$ has the formula —$(CH_2)_w$—C(O)NH—$(CH_2)_z$— or —$(CH_2)_w$—NHC(O)—$(CH_2)_z$— and $R^3$ is $R^{12}$-substituted or unsubstituted heterocycloalkyl or $R^{12}$-substituted or unsubstituted heteroaryl. The integers w and z are independently integers from 0 to 20. In other embodiments, $R^3$ is morpholino, and w and z are independently integers from 1 to 5. In some embodiments, $R^4$ and $R^5$ are joined together to form a substituted or unsubstituted adamantyl, or substituted or unsubstituted cyclohexyl. In some embodiments, $R^4$ and $R^5$ are joined together to form a $R^{14}$-substituted or unsubstituted adamantyl or $R^{14}$-substituted or unsubstituted cyclohexyl. In an exemplary embodiment, $R^4$ and $R^5$ are joined together to form a substituted or unsubstituted adamantyl. In another exemplary embodiment, $R^4$ and $R^5$ are joined together to form a $R^{14}$-substituted or unsubstituted adamantyl.

In some embodiments, $R^4$ and $R^5$ are joined together to form a $R^{14}$-substituted or unsubstituted adamantyl having the structure of Formula (IV), wherein $R^{1a}$, $R^{1b}$, $R^2$, $R^3$, $L^1$, $L^2$, $L^3$ and $Z^2$ are as defined above for Formula (II), and wherein substituent $R^{14}$ is optional.

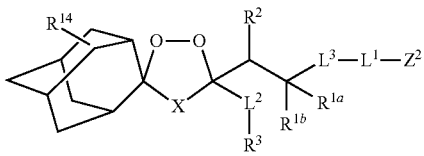

(IV)

Pharmaceutical Formulations

In another aspect, the invention provides a pharmaceutical formulation including the prodrug compound of the present invention and a pharmaceutically acceptable expedient or pharmaceutically acceptable salt thereof. In some embodiments, the pharmaceutical formulation further includes an $Fe^{II}$ containing agent.

The pharmaceutical formulations of the present invention can be prepared and administered in a wide variety of oral, parenteral and topical dosage forms. Thus, the compounds of the present invention can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable carrier or excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampules are convenient unit dosages. The compounds of the invention can also be incorporated into liposomes or administered via transdermal pumps or patches. Pharmaceutical admixtures suitable for use in the present invention are well-known to those of skill in the art and are described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60 and 80; Pluronic F-68, F-84 and P-103; cyclodextrin; polyoxyl 35 castor oil; or other agents known to those skilled in the art. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, combinations of the foregoing, and other agents known to those skilled in the art. Such agents are typically employed at a level between about 0.01% and about 2% by weight. Determination of acceptable amounts of any of the above adjuvants is readily ascertained by one skilled in the art.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

Effective Dosages

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. Determination of a therapeutically effective amount of a compound of the invention is well within the capabilities of those skilled in the art, especially in light of the detailed disclosure herein.

As is well known in the art, therapeutically effective amounts for use in humans can also be determined from animal models. For example, a dose for humans can be formulated to achieve a concentration that has been found to be effective in animals. Adjusting the dose to achieve maximal efficacy in humans based on the methods described above and other methods as are well-known in the art is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned which does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: *The Pharmacological Basis of Therapeutics*, Ch.1, p. 1, 1975. The exact formulation, route of administration and dosage can be chosen by the individual physician in view of the patient's condition and the particular method in which the compound is used.

Methods

In another aspect of the present invention, the prodrug compounds can be employed in methods to treat a disease that is associated with a cell or organism that has increased $Fe^{II}$ levels compared to $Fe^{II}$ levels in mammalian plasma. The method includes administering an effective amount of the prodrug compound (or pharmaceutical formulation thereof) to a patient in need of such treatment. Increased $Fe^{II}$ levels are cellular levels of $Fe^{II}$ that are sufficiently high to cause disease in a patient and are higher than in the plasma of a patient. In some embodiments, the method includes administering an effective amount of a prodrug compound and an $Fe^{II}$ containing agent to a patient in need of such treatment. In another embodiment, the $Fe^{II}$ containing agent is ferroglycine sulfate or transferrin. The $Fe^{II}$ containing agent may be co-administered with the prodrug. In another embodiment the $Fe^{II}$ containing agent may be administered before or after prodrug administration. A disease that is associated with a cell or organism that has increased $Fe^{II}$ levels compared to $Fe^{II}$ levels in mammalian plasma refers to a disease in which $Fe^{II}$ levels are elevated relative to $Fe^{II}$ levels in mammalian plasma in the absence of the disease. The disease associated with increased $Fe^{II}$ levels is not bound by any particular mechanistic theory, and include those diseases resulting in increase $Fe^{II}$ levels and/or caused by $Fe^{II}$ levels. Thus, in some embodiments, the increased $Fe^{II}$ levels are the result of the disease. In some embodiments, the increased $Fe^{II}$ levels are the result of the disease, and additionally the increased $Fe^{II}$ levels cause symptoms related to increased $Fe^{II}$ levels.

In some embodiments, the disease is malaria schistosomiasis, trypanosomiasis, leukemia, cervical cancer, breast cancer, colon cancer, ovarian cancer, prostate cancer, thyroid cancer, melanoma, or any cancer where transferrin receptors (CD71) are over-expressed as compared to normal cells.

In another aspect, the present invention provides a method of detecting a fluoregenic compound in a cell of an organism, by administering this fluoregenic compound to an organism, allowing the organism to metabolize the fluoregenic compound thereby producing a fluorescent compound, and detecting this fluorescent compound in a cell of a sample from this organism.

One of skill will recognize that the properties described above for the fluoregenic compound and prodrug compound are applicable to the appropriate methods and pharmaceutical compositions described herein.

General Synthetic Schemes

Compounds of this invention can be prepared in accordance with one or more of the Schemes discussed below. These procedures will be understandable to and can be carried out by someone of ordinary skill in organic chemistry. Starting materials may be prepared according to procedures provided in references below or are commercially available. Unless otherwise defined below, variables used in the Schemes are as defined in the specification or in the claims.

Scheme I

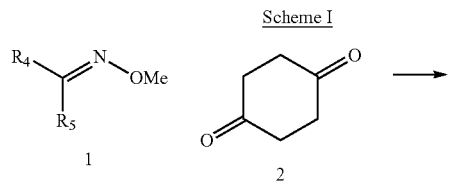

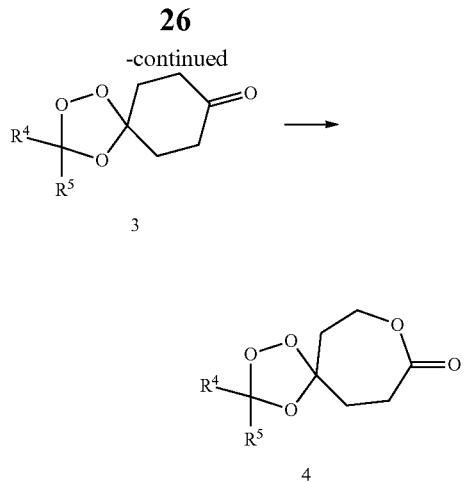

The synthetic route shown in Scheme I is a convenient method for preparing the key trioxolane lactone intermediate 4, which in turn may be elaborated as shown in later schemes to introduce various side chains and substituents $L^2$ and $R^3$. The first step of Scheme involves the Griesbaum coozonolysis of an O-alkyl oxime (1) with a ketone (e.g. 2) to afford a 1,2,4-trioxolane product 3. This reaction has been used previously for the preparation of related trioxolanes (see Griesbaum et. al. Tetrahedron, 1997, 53, 5463-5470; Vennerstrom et. al. J. Org. Chem., 1998, 63, 8582-8585; Tang et. al. J. Org. Chem., 2004, 69, 6470-6473) and typically involve bubbling ozone gas into a solution of the reactants 1 and 2 in solvents such as dichloromethane, dichloroethane, hexane, pentane, or mixtures thereof at temperatures in the range of −30° C. to 50° C., but favorably between 0-25° C. Optionally, the ketone and oxime partners can be reversed (i.e. 1 is a ketone and 2 is oxime), and in certain cases such modification may lead to improved yields of the product. Provided that $R^4$ and $R^3$ together comprise a cycle or are otherwise bulky substituents, the trioxolane products are stable and can be purified by standard methods of synthetic organic chemistry, including silica gel flash chromatography and re-crystallization. In the second step of Scheme 1, the trioxolane ketone 3 is subjected to a Baeyer-Villiger oxidation, leading to the ring-expanded lactone product 4, which is readily elaborated into various side chains comprising variables $L^2$ and $R^3$ as illustrated in Scheme II. The Baeyer-Villiger oxidation is a classic reaction in organic chemistry (see Comprehensive Organic Synthesis, 1991, 7, 671-688) and will be well known to those of ordinary skill in the art. Typically the reaction is carried out by reacting the ketone substrate with a peracid such as m-chloroperbenzoic acid or peracetic acid in solvent such as tetrahydrofuran, dioxane, or similar, at reaction temperatures of about 0° C. and 50° C.

Scheme II

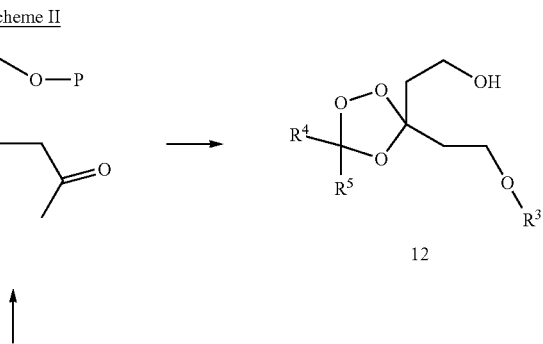

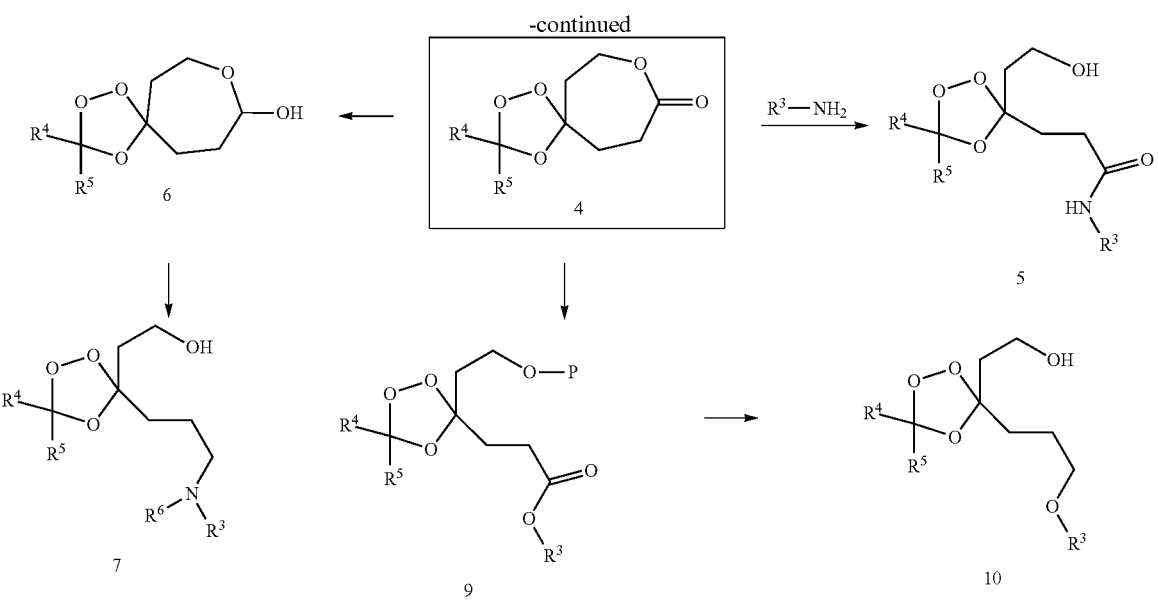

Illustrated in Scheme II are reactions that can be used to introduce various side chain substituents $L^2$ and $R^3$ in the compounds of this invention. The reactions presented in Scheme II are not intended to be comprehensive but rather represent certain possibilities that will be understandable to those of ordinary skill in the field. The modification of $L^2$ and/or $R^3$ substituents in compounds of the invention can be used to modify the physiochemical or other pharmacokinetic and toxicological properties of a prodrug. Each of the intermediates 5, 7, 8, 10, and 12 in Scheme II possess a free hydroxyl residue that can be used to introduce a drug moiety via various linker chemistries (as described in Scheme IV and V).

The reaction of lactone 4 with an amine provides amide derivatives such as 5. These reactions can be carried out in a single step by heating a solution of lactone 4 with an equivalent or favorably an excess quantity of an amine (e.g. $R^3$—$NH_2$), in a solvent such as toluene, xylene, dioxane, or acetonitrile, or using the amine itself as solvent, at temperatures ranging from 0° C. to 140° C., optionally using a sealed tube or pressure vessel, to afford the amide 5. Optionally, amides 5 can be prepared in two steps by 1) lactone hydrolysis under standard conditions (e.g. using LiOH, NaOH, KOH or similar reagent in solvents such as methanol, tetrahyrofuran, water, or mixtures thereof) and 2) reaction of the resulting carboxylic acid with an amine (e.g. $R^3$—$NH_2$) using standard carbodiimide or related bond forming reagents (EDC, DCC, HATU, HBTU, etc.).

The reaction of lactone 4 with a mild reducing reagent such as diisobutylaluminum hydride (DIBAL) in solvents such as toluene, heptane, hexane, dichloromethane, tetrahydrofuran, or mixtures thereof, and at temperatures between −100° C. and 0° C., favorably below −50° C., affords partial reduction to the aldehyde which is in equilibrium with the lactol form (6) shown in Scheme II. It will be well known by those of ordinary skill in the art that aldehydes (including lactols) can be reacted directly with phosphonium ylides (Wittig reaction) or stabilized phosphonate anions (Horner-Wadsworth-Emmons reaction) to afford olefinic products 8. Alternatively, subjecting 6 to reductive amination with an amine affords amine-containing side chains as shown for 7. Reductive amination reactions are favorably conducted in solvents such as methanol, ethanol, tetrahydrofuran, dichloroethane or mixtures thereof, using reducing agents such as sodium cyanoborohydride, or sodium triacetoxyborohydride, at temperatures generally in a range of 0° C. to 100° C. Reductive amination of carbonyl species in trioxolane-containing substrates is precedented (Vennerstrom et. al. J. Org. Chem., 2004, 69, 6470-6473).

Ether containing side chains as in compounds 10 and 12 of Scheme II can be prepared by at least two different synthetic routes. Hence, reaction of lactone 4 with an alkoxide (e.g. NaOMe or similar) to afford the ring-opened hydroxyl ester can be followed by protection of the hydroxyl function to afford 9 (P=a suitable protecting group for hydroxyl, such as trialkylsilyl, benzyl, etc.). The ester function in 9 can then be reduced to alcohol using standard reducing reagents (e.g. lithium aluminum hydride or sodium borohydride, or lithium borohydride in solvents such as tetrahydrofuran, diethyl ether or dioxane) and the protecting group (P) removed under appropriate conditions (e.g., fluoride ion for silyl ethers, hydrogenolysis for benzyl ethers) to afford alcohol 10. Reaction of lactone 4 with an alkyl lithium or Grignard reagent affords a keto alcohol and subsequent protection of the alcohol as before to afford 11. Baeyer-Villiger oxidation of the ketone function affords an acetate, alkaline hydrolysis of which serves to introduce a second alcohol function that can be converted into an ether function under standard conditions (e.g., formation of the alkoxide with a base such as sodium hydride or alkyl lithium, and reaction of the alkoxide with an alkyl, allyl, or benzylic halide). Finally, removal of the protecting group P using the relevant conditions affords the desired alcohol 12.

Scheme III

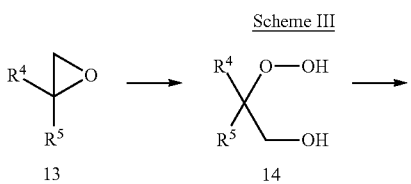

-continued

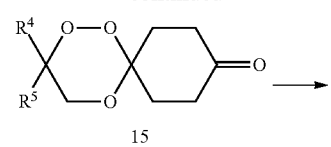

15

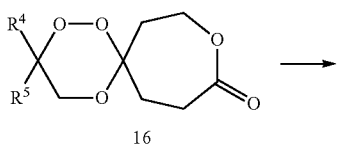

16

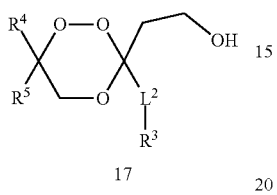

17

Compounds of the invention bearing a trioxane ring (i.e., where X=—CH$_2$—O—, or —O—CH$_2$—) can be prepared using established procedures as illustrated in Schemes III and IV. As shown in Scheme III, an epoxide 13 is reacted with hydrogen peroxide, with or without an acid catalyst, to afford a beta-hydroperoxy alcohol 14. Reactions of this type have been carried out with anhydrous hydrogen peroxide (see Kerr, B. et al, J. Chem. Soc., Chem. Commun. 1985, 590-593; Subramanyam, V. et. al., J. Chem. Soc., Chem. Commun. 1976, 508-509; Adam, W. et al, J. Org. Chem. 1997, 62, 3183-3189) or using a 50% aqueous solution of hydrogen peroxide pretreated with magnesium sulfate and employing molybdenyl acetylacetonate (MoO$_2$(acac)$_2$) as catalyst (see Tang et al, J. Org. Chem., 2005, 70, 5103-5110). Reaction of hydroperoxy alcohol 14 with a carbonyl species (e.g. cyclohexane-1,4,-dione) using standard conditions for forming acetals (e.g. catalytic para-toluenesulfonic acid, camphorsulfonic acid, methanesulfonic acid, or the like in a solvent such as dichloromethane, toluene, or the like) affords the desired trioxane intermediate 15. Ketone 15 can then be converted in two steps (via the lactone 16) to the alcohol intermediate 17, using conditions analogous to those described in the earlier Schemes for the preparation of alcohols such as 5, 7, 8, 10, and 12 from ketone 3.

Scheme IV

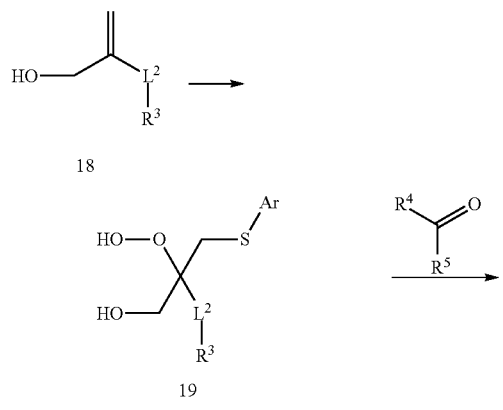

-continued

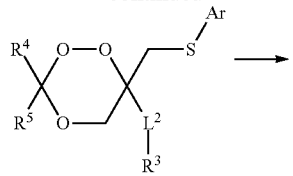

20

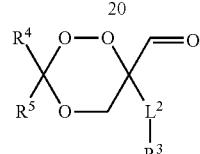

21

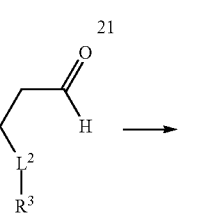

22                                23

The synthesis of regioisomeric trioxane compounds of the invention (i.e., where X=—O—CH$_2$—) is illustrated in Scheme IV. These compounds are prepared by a version of the thiol-olefin co-oxygenation reaction of substituted allylic alcohols as described in the organic chemistry literature (see O'Neill et al Org. Lett. 2004, 6, 3035-3038). In this reaction, a oxygen-saturated solution of allylic alcohol 18, an aryl thiol, and a radical initiator such as AIBN (2,2'-azobis(2-methylpropionitrile)) is irradiated with ultraviolet light. The mechanism of the reaction is thought to involve Markovnikov type addition of an arylthiyl radical to the alkene in 18, followed by trapping of the resulting tertiary carbon-centered radical by oxygen to form a peroxy radical that subsequently abstracts a hydrogen atom from the aryl thiol to generate beta-hydroperoxy alcohol 19. Reaction of 19 with a ketone under acetal-forming conditions (as described above for the preparation of 15) then affords the trioxane intermediate 20. Next, the sulfide 20 is oxidized to the sulfoxide, for example using a peracid such as m-chloroperbenzoic acid, peracetic acid, or the like in a solvent such as dichloromethane, tetrahydrofuran, or the like. The sulfoxide is then subjected to a Pummerer rearrangement (for a review see, Grierson, D. S, and Husson, H.-P. Comp. Org. Syn. 1991, 6, 924-937) to afford the aldehyde 21. The Pummerer rearrangement leading to 21 is favorably carried out according to the method of O'Neill an co-workers (referenced above), employing an activating reagent such as trifluoroacetic anhydride in the presence of a base such as lutidine, N-methylmorpholine, or the like. Aldehyde 21 can be homologated by one carbon atom to aldehyde 22 using a variety of procedures that will be familiar to those of ordinary skill in organic chemistry. Favorably, such homologations are carried out with the phosphorus ylide generated by treating (methoxymethyl)triphenylphosphonium bromide, (methoxymethyl)diphenylphosphine oxide or similar reagent with a base such as sodium hydride, lithium diisopropylamide, sodium amide or the like (see for example, Farmer et al, Bioorg. Med. Chem. Lett. 2003, 13, 261-264; Kuroda et al, Organic and Bioorganic Chemistry, 1994, 5, 521-526). The resulting enol ethers are then hydrolyzed under acidic conditions to afford the homologated aldehyde. Finally, homologated 22 can be reduced to alcohol 23 using a reducing agent such as sodium borohydride, lithium borohydride, sodium triacetoxyborohydride, or similar reagent in solvents such as methanol, tetrahydrofuran, dioxane, or mixtures thereof. Both aldehyde 22 and alcohol 23 are useful intermediates for preparing compounds of the invention, as described below.

reagents with carbonyl functions in trioxolane containing substrates has been described previously (see, J. Org. Chem., 2004, 69, 6470-6473 and PCT publication WO/2003/000676). If a second $R^1$ substituent is desirably, the oxidation and addition chemistry described above can simply be repeated to introduce a second $R^1$ substituent, affording compounds such as 28.

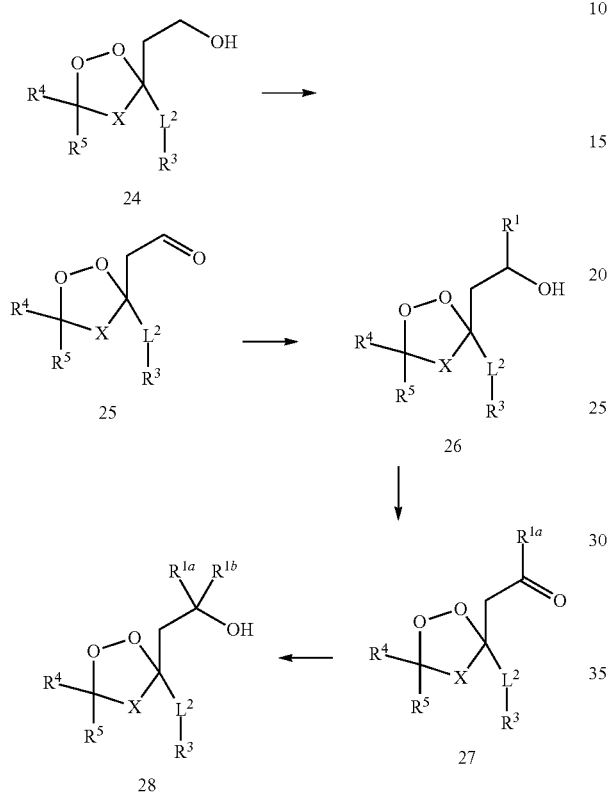

The generic structure 24 shown above in Scheme V encompasses the various alcohols 5, 7, 8, 10, 12, 17, and 23 described in Schemes II-IV above. Here we describe synthetic methods for the introduction of one or two substituents $R^1$ in compounds of the invention. Oxidation of alcohol 24 to the aldehyde 25 can be accomplished using a variety of well known methods. Hence, the group of Vennerstrom has used the Swern oxidation (for a review see Tidwell, *Synthesis*, 1990:857-870) to oxidize trioxolane containing substrates to the aldehyde (see for example, Vennerstrom et. al. *J. Org. Chem.*, 2004, 69:6470-6473). The Dess-Martin periodinane (see Boeckman, R. J. In "*Encyclopedia of Reagents for Organic Synthesis*"; Paquette, L. A., Ed.; Wiley: Chichester, UK, 1995, 7:4982-4987) is another convenient reagent for affecting the oxidation of alcohols to aldehydes or ketones. The reaction is usually conducted in dichloromethane or similar solvent at temperatures between 0° C. and 50° C., often at room temperature. Introduction of the $R^1$ substituent can be accomplished by reacting aldehyde 25 with an alkyllithium or Grignard reagent in a solvent such as tetrahydrofuran, hexane, or mixtures thereof, to afford the addition product 26, an alcohol bearing an $R^1$ substituent. Suitable organometallic reagents may include phenylmagnesium bromide or chloride, methylmagnesium bromide or chloride, vinylmagnesium bromide or chloride, methyllithium, phenyllithium, vinyllithium, or the like. Reactions of these Compounds of the invention wherein $R^2$ is an electron-withdrawing group can be synthesized as shown in Scheme VI above. The generic structure 29 is intended to represent any of the various aldehyde and ketone intermediates described above in Schemes II-V. The first step involves introduction of a bromine at the position alpha to the carbonyl function. This transformation can be accomplished using reagents such as bromine or N-bromosuccinimide (see, Boswell, G. Journal of Heterocyclic Chemistry 1996, 33(1), 33-9; De Kimpe, Norbert; Tetrahedron Letters 1980, 21, 2257-60) in solvents such as diethyl ether, DMSO, dioxane or in the like, and optionally with exposure to ultraviolet irradiation (see Arbuj, Sudhir S. Tetrahedron Letters 2007, 48, 1411-1415). Next, the bromine atom is displaced by cyanide anion (see, Carabateas, Philip M. et al Journal of Heterocyclic Chemistry 1984, 21, 1849-56) using sodium cyanide, potassium cyanide, or equivalent reagent, in a solvent such as dimethyl sulfoxide, dimethylformamide, ethanol, or the like at temperatures of around 0° C. to 120° C. to afford 31. Finally, the ketone 31 can be reduced to the alcohol 32 using a reducing agent such as sodium borohydride, lithium borohydride, sodium triacetoxyborohydride, or the like in solvents such as methanol, tetrahydrofuran, dioxane, or mixtures thereof. Both carbonyl species 31 and alcohol 32 are useful intermediates for preparing compounds of the invention, as described below.

and purified by standard methods such as silica gel flash chromatography. Intermediate 35 is then reacted with an amine or alcohol containing drug to form 36. These reactions are favorably carried out in solvents such as dichloromethane, acetonitrile, DMF, or the like, at temperatures between around 0° C. to 100° C. until reaction is complete. In some

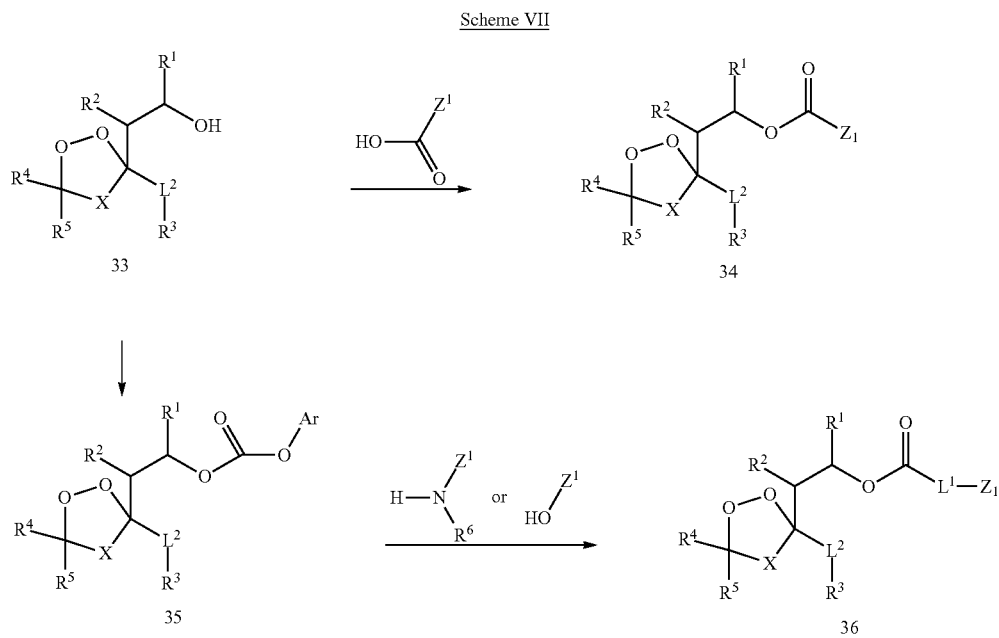

All of the various alcohol intermediates described in the above Schemes, with or without $R^1$ or $R^2$ substituents, are represent in Scheme VII generically as alcohol 33. Illustrated in Scheme VII is the attachment of a drug species to 33 via acid, carbonate, or carbamate functionality. First, the attachment of a carboxylic acid bearing drug species to 33 can be accomplished directly via the formation of an ester bond as in 34. This process will be well known to those of ordinary skill in the art and can be accomplished with carbodiimide or related coupling reagents (e.g., DCC, EDC, HATU, and the like). Alternatively, the carboxylic acid function can be activated in an initial step, for example by forming the acid chloride or pentafluorophenyl ester, followed by reaction with 33 or with the corresponding alkoxide form of 33 generated by reaction with a base such as sodium hydride, butyllithium or the like. Acid chlorides are conveniently prepared by reaction of the acid with reagents such as thionyl chloride, oxallyl chloride, or the like. Pentafluorophenyl esters are conveniently prepared by reaction of the acid with pentafluorophenyl trifluoroacetate in a solvent such as acetonitrile, dichloroethane, DMF, or the like.

For drug species bearing a hydroxyl or amine function, the conjugation to 33 can be made in the form of a carbonate or carbamate function, respectively. First, the alcohol 33 is activated with a reagent such as 4-nitrophenyl chloroformate, phosgene, triphosgene, carbonyl imidazole or the like. Reactions of this type are favorably carried out in solvent such as dichloromethane, acetonitrile, or the like, in the presence of an acid-scavenging base such as triethylamine, diisopropylethylamine, or the like, and optionally with the addition of a nucleophilic promoter such as 4-dimethylaminopyridine. Reaction of 33 with 4-nitrophenyl chloroformate as described above affords the carbonate 35, which usually can be isolated cases, reactions of this type may be promoted with additives such as 4-dimethylaminopyridine. An alternative approach applicable to amine-bearing drugs is to convert the amine function into an isocyanate, using methods that will be familiar to those skilled in the art (e.g. reaction with phosgene, triphosgene, or the like). The isocyanate is then reacted with alcohol 33, for example by heating in a solvent such as toluene, acetonitrile, dichloroethane, or the like, at a temperature of around 0° C. to 120° C. until carbamate formation is complete. Final products 36 can be purified using standard methods of synthetic organic chemistry, including silica gel flash chromatography, high-performance liquid chromatography, recrystallization, and the like.

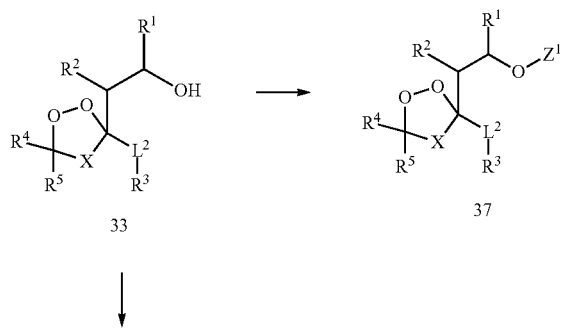

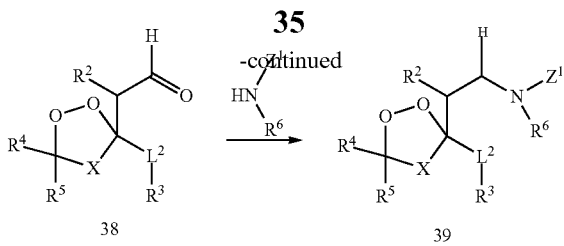

Compounds of the invention bearing an ether linkage to $Z^1$ can be prepared as shown in Scheme VIII by reacting alcohol 33, or alternatively the alkoxide form of 33 (prepared as described above) with an electrophilic moiety such as $Z^1$-LG, wherein LG is a leaving group such as bromo, iodo, methanesulfonyl, toluenesulfonyl, or the like. These nucleophilic displacement reactions will be well known to those of ordinary skill in organic chemistry and are favorably carried out in solvents such as acetonitrile, dimethylsulfoxide, dimethylformamide, or the like at reaction temperatures of about −25° C. to 120° C.

Amine containing drugs can also be conjugated directly to the trioxolane moiety as shown in Scheme VIII. Oxidation of alcohol 33 to the corresponding aldehyde 38 is favorably carried out using the Dess-Martin periodinane, in a solvent such as dichloromethane, or the like, at temperatures between 0° C. and 50° C. Other methods to oxidize alcohols to aldehydes are also available and will be familiar to those of ordinary skill in organic chemistry. Next, a reductive amination reaction is carried out with aldehyde 38, an amine containing drug, and a suitable reducing agent such as sodium triacetoxyborohydride, sodium cyanoborohydride, or the like to afford 39. Reductive amination is a well established reaction in organic chemistry (for a discussion of favorable reaction conditions see Abdel-Magid et al, J. Org. Chem., 1996, 61, 3849-3862) and has been successfully applied previously in reactions of trioxolane-containing carbonyl substrates (Vennerstrom et. al. J. Org. Chem., 2004, 69, 6470-6473).

EXAMPLES

Example 1

Preparation of 2-(5,5-spiroadamantyl-3-(3-(2-morpholinoethylamino)-3-oxopropyl)-1,2,4-trioxolan-3-yl)ethyl-2,5-dichlorophenylcarbamate

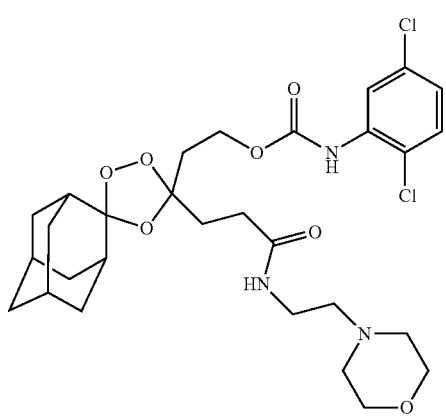

Step 1: Preparation of O-methyl 2-adamantanone oxime

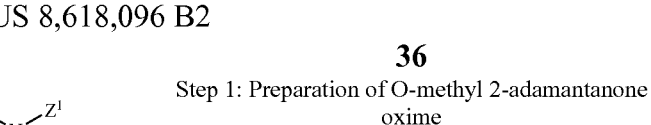

2-Adamantanone (1.3 g, 10 mmol) and methoxyamine hydrochloride (1.3 g, 15.56 mmol) were dissolved in methanol (30 ml). To this solution was added pyridine (1.5 ml, 18.5 mmol) and the reaction was stirred for 2 days. The solvent was evaporated to afford a viscous liquid which was then dissolved in dichloromethane. The organic layer was washed successively with 1N HCl (30 ml), brine (30 ml) dried with MgSO₄, filtered, and evaporated to afford a white colored crystalline solid. Yield: 1.5 g (83%). MS (m/z): (M+H)=180.

Step 2: Preparation of adamantane-2-spiro-3'-8'-oxo-1',2',4'-trioxaspiro[4.5]decane

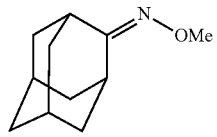

O-methyl 2-adamantanone oxime (4.5 g, 25 mmol) and 1,4 cyclohexanedione (5.6 g, 50 mmol) were dissolved in a solvent mixture of pentane:dichloromethane (1:1.5). The flask was cooled to 0° C. and ozone gas was bubbled through the reaction mixture for 1 hr. The reaction was monitored using TLC (10% ethyl acetate:hexane). After completion the solvent was evaporated and the residue purified immediately using silica gel chromatography (10% ethyl acetate:hexane) to afford the title compound as a white solid. Yield: 2.0 g (29%). MS (m/z): (M+Na⁺)=301.

Step 3: Preparation of adamantane-2-spiro-3'-9'-oxo-1',2',4',8'-tetraoxaspiro[4.6]undecane

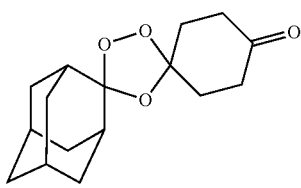

Adamantane-2-Spiro-3'-8'-oxo-1',2',4'-trioxaspiro[4.5]decane (1.0 g, 3.59 mmol) was dissolved in anhydrous dichloromethane (100 ml). To this solution was added m-chloroperoxybenzoic acid (1.76 g, 7.89 mmol) and NaHCO₃ (0.6 g, 7.18 mmol). The reaction was stirred for 48 hrs under argon after which it was quenched with water (40 ml). The water layer was extracted with dichloromethane (10 ml). The organic layers were combined and washed with saturated aqueous NaHCO₃ (100 ml) and brine (2×50 ml), and then dried (Na₂SO₄), filtered, and evaporated to afford an oil. The oil was purified using silica gel chromatography (10% ethyl acetate-hexane) to give a white colored solid. Yield: 0.60 g (60%). MS (m/z): (M+H)=294.

Step 4: Preparation of 3-(3-(2-hydroxyethyl)-5,5-spiroadamantyl-1,2,4-trioxolan-3-yl)-N-(2-morpholinoethyl)propanamide

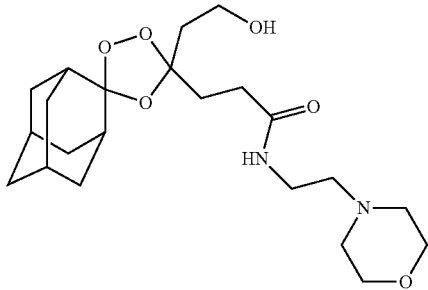

44

Adamantane-2-spiro-3'-9'-oxo-1',2',4',8'-tetraoxaspiro [4.6]undecane (100 mg, 0.340 mmol) was dissolved in a minimal amount of toluene. To this solution, 4-(2-Aminoethyl) morpholine (88.4 mg, 0.680 mmol) was added and the reaction mixture was stirred overnight at 50° C. The solvent was evaporated and the residue was dissolved in dichloromethane (10 ml). The organic layer washed with water, dried ($Na_2SO_4$), filtered, and evaporated to afford yellow colored oil. This was further purified using silica gel chromatography (0-10% MeOH—$CH_2Cl_2$). Yield: 100 mg (70%). MS (m/z): (M+H)=425.

Step 5: Preparation of 2-(5,5-spiroadamantyl-3-(3-(2-morpholinoethylamino)-3-oxopropyl)-1,2,4-trioxolan-3-yl)ethyl 2,5-dichlorophenylcarbamate A solution of 3-(3-(2-hydroxyethyl)-5,5-spiroadamantyl-1,2,4-trioxolan-3-yl)-N-(2-morpholinoethyl)propanamide (65 mg, 0.152 mmol) in toluene (2 ml) was treated with 2,5-dichlorophenyl isocyanate (43 mg, 0.228 mmol). The reaction mixture was stirred for 1 hr. The solvent was then evaporated and the residue purified by silica gel chromatography (0-10% MeOH—$CH_2Cl_2$) to afford the title compound. Yield: 80 mg (87%). MS (m/z): [M+H]=613.

Example 2

Preparation of 2-(5,5-spiroadamantyl-3-(3-(2-morpholinoethylamino)-3-oxopropyl)-1,2,4-trioxolan-3-yl)ethyl 4-phenylpiperazine-1-carboxylate

45

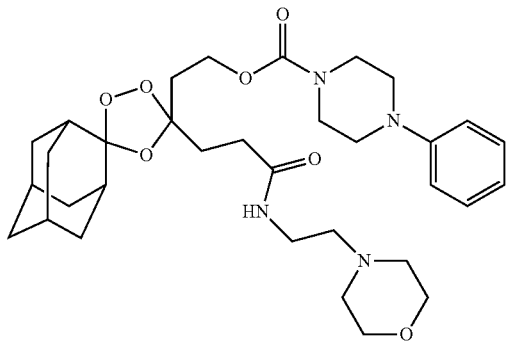

Step 1. Preparation of 2-(5,5-spiroadamantyl-3-(3-(2-morpholinoethylamino)-3-oxopropyl)-1,2,4-trioxolan-3-yl)ethyl 4-nitrophenyl carbonate A solution of 3-(3-(2-hydroxyethyl)-5,5-spiroadamantyl-1,2,4-trioxolan-3-yl)-N-(2-morpholinoethyl)propanamide (310 mg, 0.729 mmol) in anhydrous dichloromethane (25 ml) was treated with triethylamine (202 µl, 1.45 mmol), p-nitrophenyl chloroformate (294 mg, 1.45 mmol) and dimethylaminopyridine (89 mg, 0.729 mmol). The reaction mixture was stirred under argon for 4 hrs after which time the reaction mixture was washed thrice with 20 mL saturated aqueous $NaHCO_3$, dried ($Na_2SO_4$), filtered, and evaporated to afford an oil. The oil was further purified using silica gel chromatography (0-5% MeOH—$CH_2Cl_2$) to afford a yellow solid. Yield: 300 mg (70%). MS (m/z): (M+H)=590.

Step 2. Preparation of 2-(5,5-spiroadamantyl-3-(3-(2-morpholinoethylamino)-3-oxopropyl)-1,2,4-trioxolan-3-yl)ethyl 4-phenylpiperazine-1-carboxylate To a solution of 2-(5,5-spiroadamantyl-3-(3-(2-morpholinoethylamino)-3-oxopropyl)-1,2,4-trioxolan-3-yl)ethyl 4-nitrophenyl carbonate (162 mg, 0.275 mmol) in anhydrous dichloromethane (25 ml) was added 4-phenylpiperazine (42 µl, 0.275 mmol) and 4-dimethylaminopyridine (34 mg, 0.28 mmol). The reaction mixture was stirred overnight under argon. The solvent was then evaporated and the crude mixture was purified using silica-gel chromatography (0-5% MeOH—$CH_2Cl_2$) to afford the title compound. Yield: 40 mg (25%). MS (m/z): (M+H)=614.

Example 3

Preparation of 2-(5,5-adamantyl-3-(3-(2-morpholinoethylamino)-3-oxopropyl)-1,2,4-trioxolan-3-yl) ethyl phenyl carbonate

46

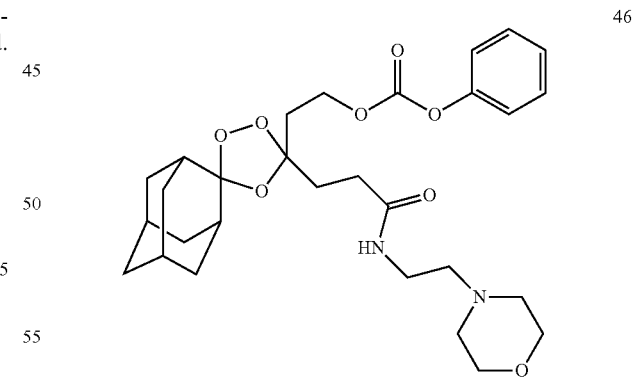

A solution of 2-(5,5-spiroadamantyl-3-(3-(2-morpholinoethylamino)-3-oxopropyl)-1,2,4-trioxolan-3-yl)ethyl 4-nitrophenyl carbonate (16 mg, 0.027 mmol) in anhydrous dichloromethane (1 ml) was treated with phenol (2.6 mg, 0.027 mmol) and 4-dimethyl aminopyridine (2 mg, 0.027 mmol) and the reaction was stirred at 50° C. under argon for 4 hrs. The reaction mixture was diluted with more dichloromethane and washed with saturated aqueous $NaHCO_3$, dried ($Na_2SO_4$), filtered, and evaporated. The residue was purified using silica-gel chromatography (0-5% MeOH—CH₂Cl₂) to afford the title compound. Yield: 10 mg (68%). MS (m/z): (M+H)=545.

Example 4

Preparation of 2-(5,5-spiroadamantyl-3-(3-(2-morpholinoethylamino)-3-oxopropyl)-1,2,4-trioxolan-3-yl)ethyl benzyl(methyl)carbamate

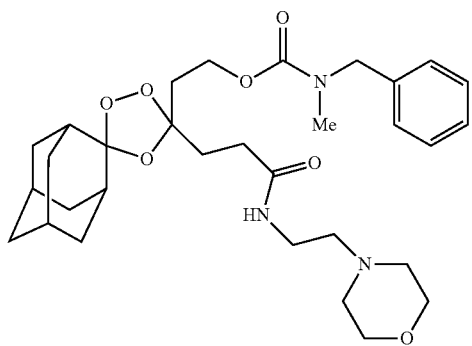

To a solution of 2-(5,5-spiroadamantyl-3-(3-(2-morpholinoethylamino)-3-oxopropyl)-1,2,4-trioxolan-3-yl)ethyl 4-nitrophenyl carbonate (25 mg, 0.042 mmol) in anhydrous dichloromethane (1 ml) was added N-methylbenzylamine (5 mg, 0.042 mmol) and 4-dimethylaminopyridine (5 mg, 0.042 mmol) and the reaction mixture stirred overnight under argon. The reaction mixture was diluted with additional dichloromethane and the solution washed with saturated aqueous NaHCO₃, dried (Na₂SO₄), filtered, and concentrated to afford yellow residue. The residue was further purified using silica-gel chromatography (0-5% MeOH—CH₂Cl₂). Yield: 10 mg (42%). MS (m/z): (M+H)=572.

Example 5

Preparation of 2-(5,5-spiroadamantyl-3-(3-(2-morpholinoethylamino)-3-oxopropyl)-1,2,4-trioxolan-3-yl)ethyl 3-(7-chloroquinolin-4-ylamino)propyl(furan-2-ylmethyl)carbamate

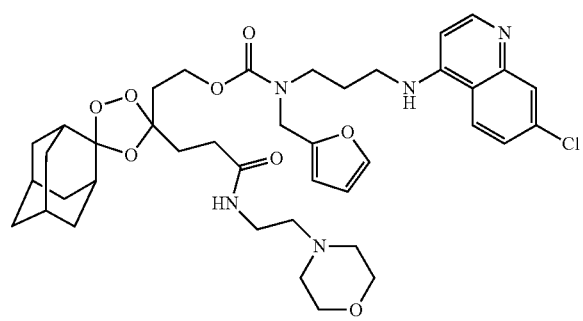

The dihydrochloride salt of N1-(7-chloroquinolin-4-yl)-N3-(furan-2-ylmethyl)propane-1,3-diamine (10 mg, 0.031 mmol, prepared as described in J. Med. Chem., 2006, 49, 4535-4543) was dissolved in anhydrous DMF (6 mL) and diisopropylethylamine (11 ul, 0.06 mmol). The solution was stirred for ten minutes and treated with 2-(5,5-spiroadamantyl-3-(3-(2-morpholinoethylamino)-3-oxopropyl)-1,2,4-trioxolan-3-yl)ethyl 4-nitrophenyl carbonate (18 mg, 0.03 mmol) and 4-dimethylaminopyridine (3.6 mg, 0.03 mmol). The reaction mixture was stirred overnight under argon. The organic layer was then diluted with dichloromethane and washed with saturated aqueous NaHCO₃, dried (Na₂SO₄), filtered, and evaporated to afford an oil. The oil was purified using HPLC (AcCN:H₂O: 0.05% TFA), the relevant fractions collected and lyophilized to afford a white powder. Yield: 9 mg (48%). MS (m/z): (M+H)=767.

Example 6

Preparation of 2-(5,5-spiroadamantyl-3-(3-(2-morpholinoethylamino)-3-oxopropyl)-1,2,4-trioxolan-3-yl)ethyl 4-methyl-2-oxo-2H-chromen-7-ylcarbamate

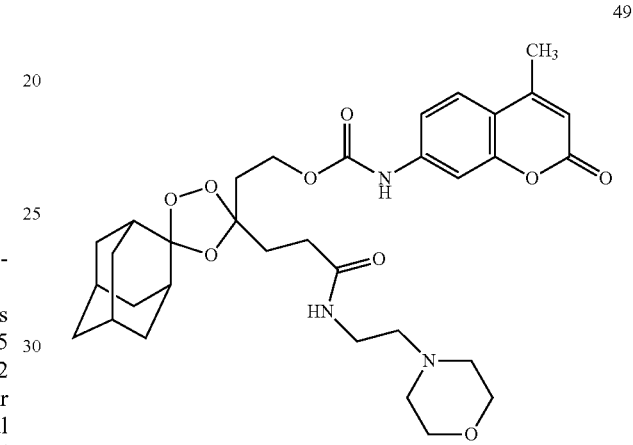

Step 1: Preparation of 7-isocyanato-4-methyl-2H-chromen-2-one

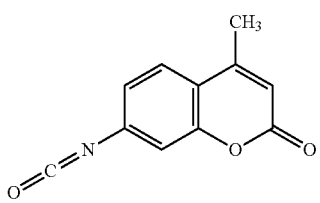

A round bottom flask was charged with 7-amino-4-methyl-coumarin (50 mg, 0.285 mmol) under argon and treated with a 20% phosgene in toluene solution (2 ml) under. The reaction mixture was heated at reflux for 15 hrs under argon during which time a white solid precipitated out of solution. After cooling, the excess phosgene was removed by bubbling argon gas through from the solution for 10 minutes. The reaction mixture was then evaporated to afford the product as white solid, which was used directly in the next step. Yield: 50 mg (87%).

Step 2: Preparation of 2-(5,5-spiroadamantyl-3-(3-(2-morpholinoethylamino)-3-oxopropyl)-1,2,4-trioxolan-3-yl)ethyl 4-methyl-2-oxo-2H-chromen-7-ylcarbamate To a solution of 3-(3-(2-hydroxyethyl)-5,5-spiroadamantyl-1,2,4-trioxolan-3-yl)-N-(2-morpholinoethyl)propanamide (60 mg, 0.041 mmol) in anhydrous THF (2 ml) was added a solution of 7-isocyanato-4-methyl-2H-chromen-2-one (57 mg, 0.28 mmol) in THF (3 mL). The reaction mixture was stirred overnight at room temperature. The solvent was then evaporated and the residue purified using silica-gel chromatography (0-5% MeOH—$CH_2Cl_2$). Yield: 45 mg (51%). MS (m/z): (M+H)=626.

Example 7

Preparation of 2-(5,5-spiroadamantyl-3-(3-(2-morpholinoethylamino)-3-oxopropyl)-1,2,4-trioxolan-3-yl)ethyl 7-nitrobenzo[c][1,2,5]oxadiazol-4-yl-carbamate

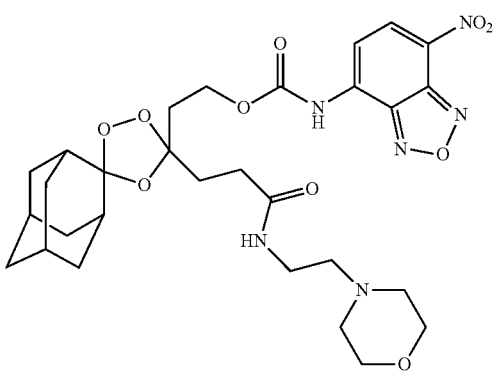

51

Step 1: Preparation of 7-amino-4-nitro-1,2,5-benzoxadiazole

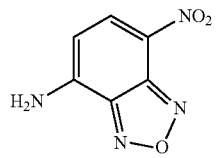

52

A solution of 4-chloro-7-nitro-1,2,5-benzoxadiazole (100 mg, 0.50 mmol) in methanol (5 ml) was treated with a solution of ammonia in methanol (5 ml of 2.0 M solution) and stirred overnight. The precipitate was filtered and the filtrate evaporated to afford a brown colored solid. This material was purified using silica gel chromatography (3:2 ethyl acetate-hexane) to afford the title compound. Yield: 60 mg, (66%).

Step 2: Preparation of 2-(5,5-spiroadamantyl-3-(3-(2-morpholinoethylamino)-3-oxopropyl)-1,2,4-trioxolan-3-yl)ethyl 7-nitrobenzo[c][1,2,5]oxadiazol-4-ylcarbamate A solution of 2-(5,5-spiroadamantyl-3-(3-(2-morpholinoethylamino)-3-oxopropyl)-1,2,4-trioxolan-3-yl)ethyl 4-nitrophenyl carbonate (50 mg, 0.08 mmol) in anhydrous dichloromethane (1 ml) was treated with 7-amino-4-nitro-1,2,5-benzoxadiazole (16 mg, 0.12 mmol) and 4-dimethylaminopyridine (10.4 mg, 0.08 mmol). The reaction was stirred overnight under argon after which the solution was diluted with dichloromethane and washed with saturated aqueous $NaHCO_3$, dried ($Na_2SO_4$), filtered, and evaporated. The residue obtained was purified using silica gel chromatography (0-10% MeOH—$CH_2Cl_2$) to afford the title compound. Yield: 25 mg (47%). MS (m/z): (M+H)=632.

Example 8

Preparation of 3-(5,5-spiroadamantyl-3-(2-(3-(7-nitrobenzo[c][1,2,5]oxadiazol-4-ylamino)propylamino)-2-oxoethyl)-1,2,4-trioxolan-3-yl)-N-(2-morpholinoethyl)propanamide

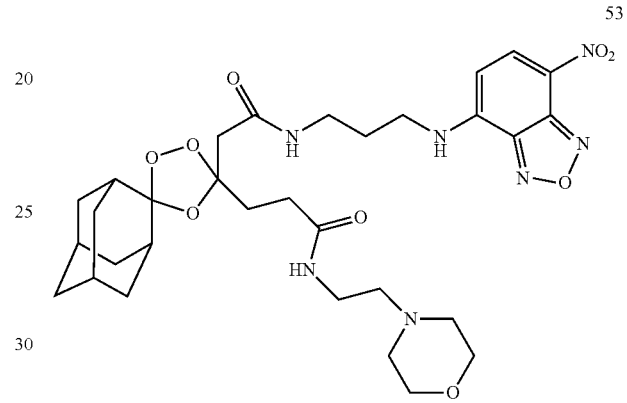

53

Step 1: Preparation of 3-(5,5-spiroadamantyl-3-(2-oxoethyl)-1,2,4-trioxolan-3-yl)-N-(2-morpholinoethyl)propanamide

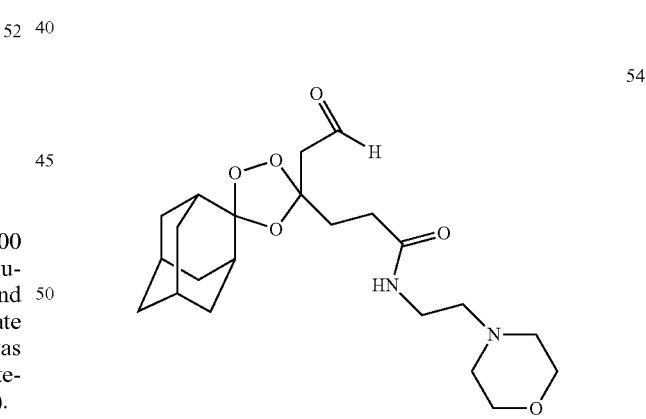

54

A solution of 3-(3-(2-hydroxyethyl)-5,5-spiroadamantyl-1,2,4-trioxolan-3-yl)-N-(2-morpholinoethyl)propanamide (100 mg, 0.235 mmol) in dichloromethane (1 ml) was treated with the Dess-Martin periodinane (150 mg, 0.352 mmol). The reaction was stirred for 1.5 hr after which it was diluted with dichloromethane (5 ml). The white precipitate obtained was filtered and the solvent was evaporated. The residue was treated with dichloromethane (5 ml), the un-dissolved solids filtered off, and the filtrate evaporated. The resulting residue was subjected to silica gel chromatography (0-10% MeOH: dichloromethane) to afford 3-(5,5-spiroadamantyl-3-(2-oxoethyl)-1,2,4-trioxolan-3-yl)-N-(2-morpholinoethyl)propanamide. MS (m/z): (M+H)=423.

Step 2: Preparation of 2-(5,5-spiroadamantyl-3-(3-(2-morpholinoethylamino)-3-oxopropyl)-1,2,4-trioxolan-3-yl)acetic acid

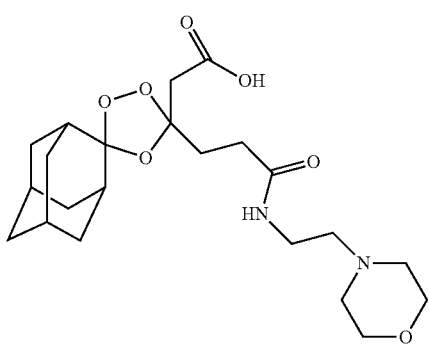

55

The 3-(5,5-spiroadamantyl-3-(2-oxoethyl)-1,2,4-trioxolan-3-yl)-N-(2-morpholinoethyl) propanamide prepared in step 1 was immediately dissolved in a mixture of tert-butanol-water (5:1, 6 mL) and the reaction mixture cooled to 0° C. Next, a 2.0 M isobutylene solution in THF (0.5 mL) was added, followed by $Na_2HPO_4$ (94 mg, 0.685 mmol) and $NaClO_2$ (64 mg, 0.71 mmol). The reaction mixture was stirred for 3 hrs at 0° C. The solvent was evaporated and the residue purified by HPLC (0.05 TFA: AcCN: $H_2O$). The relevant fractions were collected and lyophilized to afford a white powder. Yield: 60 mg (58%). MS (m/z): (M+H)=439.

Step 3: Preparation of N1-(7-nitro-[1,2,5]benzoxadiazol-4-yl)propane-1,3-diamine

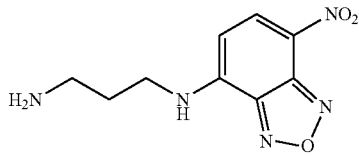

56

4-Chloro-7-nitro-[1,2,5]benzoxadiazole (100 mg, 0.501 mmol) was dissolved in methanol (5 ml). N-Boc-1,3-propanediamine (44 mg, 0.25 mmol) was then added and the reaction mixture stirred overnight. The solvent was evaporated and the residue was purified using silica gel chromatography with ethyl acetate:hexane (1:1) to afford dark brown solid. This material was then treated with a solution of 4.0 M HCl in dioxane (excess) overnight to remove the Boc group. The solution was evaporated to afford $N^1$-(7-nitro-[1,2,5]benzoxadiazol-4-yl)propane-1,3-diamine as the hydrochloride salt, which was used without further purification. Yield: 60 mg (51%). MS (m/z): (M+H)=237.22.

Step 4: Preparation of 3-(5,5-spiroadamantyl-3-(2-(3-(7-nitrobenzo[c][1,2,5]oxadiazol-4-ylamino)propylamino)-2-oxoethyl)-1,2,4-trioxolan-3-yl)-N-(2-morpholinoethyl) propanamide A mixture of 2-(5,5-spiroadamantyl-3-(3-(2-morpholinoethylamino)-3-oxopropyl)-1,2,4-trioxolan-3-yl)acetic acid (10 mg, 0.022 mmol) and $N^1$-(7-nitro-[1,2,5]benzoxadiazol-4-yl) propane-1,3-diamine hydrochloride (5.2 mg, 0.022 mmol) was dissolved in DMF. The reaction mixture was then treated with 1-ethyl-3-(3-dimethylaminopropyl)-carbodiimide (13 mg, 0.066 mmol), N-hydroxybenztriazole (9 mg, 0.066 mmol), and diisopropylethylamine (24 µl, 0.132 mmol) and stirred overnight under argon. The solvent was then evaporated and the residue dissolved in dichloromethane. The organic layer was then washed with water, dried (Na2SO4), filtered, and evaporated to afford an oil. This material was purified using silica gel chromatography (0-5% MeOH—$CH_2Cl_2$) to afford the title compound. Yield: 8 mg (55%). MS (m/z): (M+H)=658

Example 9

Preparation of 3-(3-(2-(benzylamino)ethyl)-5,5-spiroadamantyl-1,2,4-trioxolan-3-yl)-N-(2-morpholinoethyl)propanamide

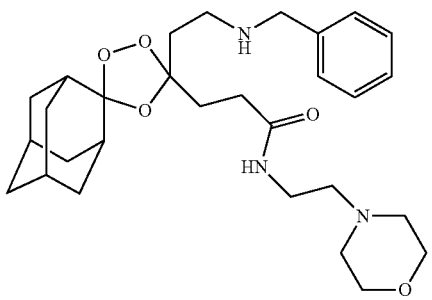

57

A solution of 3-(5,5-spiroadamantyl-3-(2-oxoethyl)-1,2,4-trioxolan-3-yl)-N-(2-morpholinoethyl)propanamide (50 mg, 0.059 mmol) was dissolved in anhydrous dichloroethane (1 ml) and treated with benzylamine (10 µl, 0.088 mmol) and sodium triacetoxy borohydride (25 mg, 0.118 mmol). The reaction mixture was stirred for 1 hr at room temperature. The solvent was evaporated and the residue was redissolved in dichloromethane. The solution was then washed with saturated aqueous $NaHCO_3$ solution, dried ($Na_2SO_4$), filtered, and evaporated to afford an oil. MS (m/z): (M+H)=514.

Example 10

Preparation of 3-(3-(2-hydroxyethyl)-5,5-spiroadamantyl-1,2,4-trioxolan-3-yl)-N-(3-(2-oxopyrrolidin-1-yl)propyl)propanamide

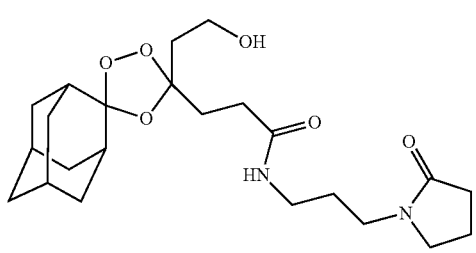

58

Adamantane-2-spiro-3'-9'-oxo-1',2',4',8'-tetraoxaspiro[4.6]undecane (160 mg, 0.55 mmol) was dissolved in the minimum amount of toluene. To this solution was added 1-(3-aminopropyl)-2-pyrrolidinone (152 µl, 1.11 mmol) and the reaction mixture was stirred at 50° C. for 5 hrs. The solvent was evaporated and the residue was dissolved in dichloromethane (10 ml). The organic layer was washed with water, dried (Na₂SO₄), filtered, and evaporated to afford a yellow oil. The crude alcohol was purified using silica gel chromatography (0-10% MeOH—CH₂Cl₂). Yield: 153 mg (64%). MS (m/z): (M+H)=437.

Example 11

Preparation of Cmpd 61, 2-(5,5-spiroadamantyl-3-(3-(2-morpholinoethylamino)-3-oxopropyl)-1,2,4-trioxolan-3-yl)-1-phenylethyl-2,5-dichlorophenylcarbamate

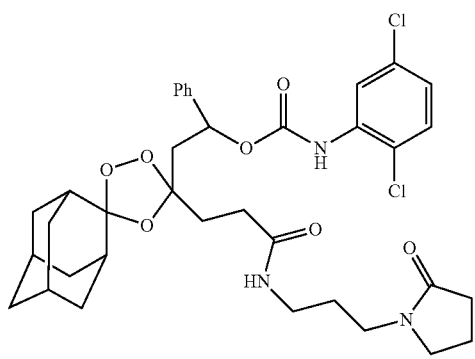

61

Step 1: Preparation of Cmpd 59, 3-(3-(2-oxoethyl)-5,5-spiroadamantyl-1,2,4-trioxolan-3-A-N-(3-(2-oxopyrrolidin-1-yl)propyl)propanamide

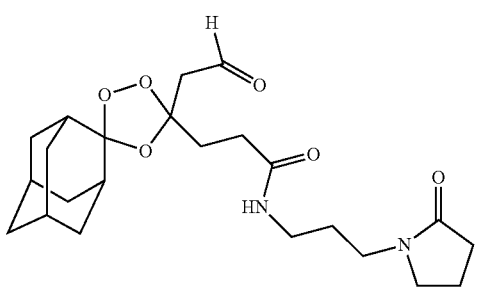

59

A solution of 3-(3-(2-hydroxyethyl)-5,5-spiroadamantyl-1,2,4-trioxolan-3-yl)-N-(3-(2-oxopyrrolidin-1-yl)propyl) propanamide (Cmpd 58, 0.20 g) in 2 mL of dichloromethane was treated with Dess-Martin periodinane (0.29 g) and stirred at room temperature for 30 minutes. The reaction mixture was quenched by addition of 10 mL of 1:1 saturated aqueous NaHCO₃ and saturated aqueous NaS₂O₃. The mixture was stirred until organic and aqueous phases became clear and then the layers were separated and the aqueous phase extracted twice with diethyl ether (10 mL). The combined organic layers were dried over Na2SO4, filtered and concentrated to afford the Cmpd 59 (0.15 g), which was used without further purification.

Step 2: Preparation of Cmpd 60, 3-(3-(2-hydroxy-2-phenylethyl])-5,5-spiroadamantyl-1,2,4-trioxolan-3-yl)-N-(3-(2-oxopyrrolidin-1-yl)propyl)propanamide

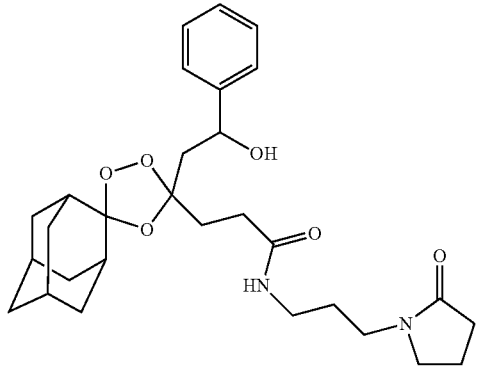

60

A solution of phenyl magnesium bromide (1.1 mL, 1.0 M in tetrahydrofuran) was added to a dry flask maintained at −78° C. A solution of Cmpd 59 (160 mg in 3 mL of anhydrous tetrahydrofuran) was then added drop wise. The reaction mixture was stirred for 3 hr under argon at −78° C. and was then quenched by adding saturated ammonium chloride solution (3 mL). The resultant mixture was maintained for 1 hour at room temp. The reaction was diluted with dichloromethane (10 mL) and the aqueous layer separated. The aqueous layer was washed with dichloromethane (2 mL). The organic layers were combined, dried (Na₂SO₄), filtered and evaporated to afford an oil. The crude oil was purified by silica gel chromatography (5% methanol-ethyl acetate) to afford the title compound. Yield: 74 mg (40%). MS (m/z): (M+H)=514.

Step 3: Preparation of Cmpd 61

A solution of Cmpd 60 (40 mg, 0.097 mmol) in anhydrous toluene (2 mL) was treated with 2,5-dichlorophenyl isocyanate (36 mg, 0.194 mmol). See Example 1. The reaction mixture was stirred at 50° C. overnight. The solvent was then evaporated and the residue purified by silica gel chromatography (0-5% methanol-ethyl acetate) to afford the title compound. Yield: 30 mg (60%). MS (m/z): [M+H]=701.

Example 12

Preparation of (Cmpd 64), 2-(5,5-spiroadamantyl-3-(3-(2-morpholinoethylamino)-3-oxopropyl)-1,2,4-trioxolan-3-yl)-1-phenylethyl-2,5-dichlorophenylcarbamate

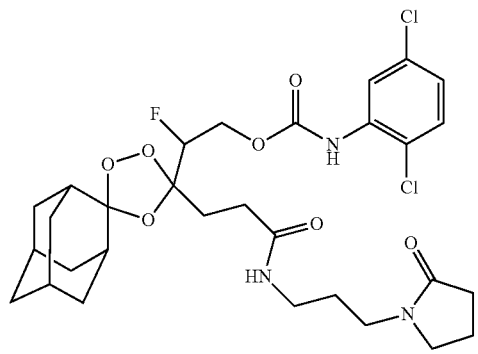

64

Step 1: Preparation of fluoroaldehyde Cmpd 62, 3-(3-(1-fluoro-2-oxoethyl)-5,5-spiroadamantyl-1,2,4-trioxolan-3-yl)-N-(3-(2-oxopyrrolidin-1-yl)propyl)propanamide

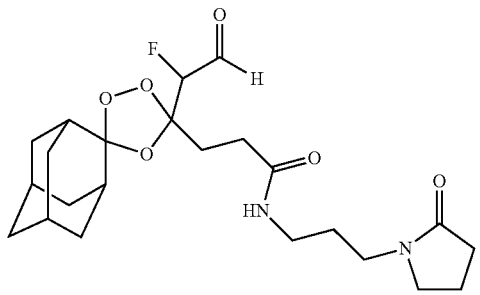

62

Aldehyde Cmpd 59 (20 mg, 0.045 mmol) was dissolved in anhydrous dimethylformamide (0.5 mL) and the solution cooled to ca. 5° C. SELECTFLUOR® (24 mg, 0.0675 mmol) was added to the reaction mixture, followed by L-proline (1.5 mg, 0.0135 mmol). The reaction mixture was stirred at ca. 5° C. for 30 min after which it was diluted with water (5 mL). The aqueous layer was extracted with ethyl acetate (5 mL). The organic layers were combined, dried (Na2SO4), filtered and evaporated to afford the crude Cmpd 62, which was used in the next step without further purification. MS (m/z): (M+H)=454.

Step 2: Preparation of Cmpd 63, 3-(3-(1-fluoro-2-hydroxyethyl)-5,5-spiroadamantyl-1,2,4-trioxolan-3-yl)-N-(3-(2-oxopyrrolidin-1-yl)propyl)propanamide

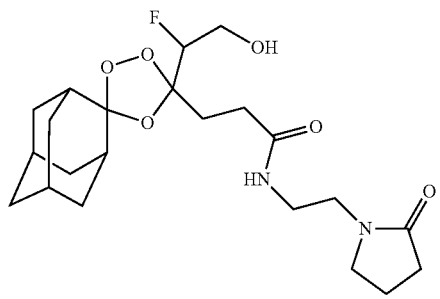

63

Fluoroaldehyde Cmpd 62 (10 mg, 0.022 mmol) was dissolved in a mixture of dichloromethane (0.5 mL) and ethanol (0.25 mL). Sodium borohydride (2 mg, 0.044 mmol) was added and the reaction was stirred for 30 min. Saturated ammonium chloride (1 mL) was added and the reaction mixture was stirred for additional 30 min. The reaction was then diluted with dichloromethane (1 mL) and the organic layer was separated, washed with saturated NaHCO3, dried (Na2SO4), filtered and concentrated. The residue obtained was further purified using silica gel chromatography (5% methanol-dichloromethane) to afford the title compound. Yield: 6 mg (65%). MS (m/z): (M+H)=456

Step 3: Preparation of Cmpd 64

A solution of alcohol Cmpd 63 (23 mg, 0.05 mmol) in DMF (0.5 mL) was treated with 2,5-dichlorophenyl isocyanate (20 mg, 0.1 mmol). The reaction mixture was stirred overnight at room temperature. Next, water (5 mL) was added to the reaction mixture and the solution extracted with ethyl acetate. The organic layer was dried (Na2SO4), filtered and concentrated. The residue was purified using preparative HPLC (0.05% TFA:ACN:H2O) to afford Cmpd 64. Yield: 2 mg (25%). MS (m/z): (M+H)=643

Example 13

Preparation of Cmpd 72

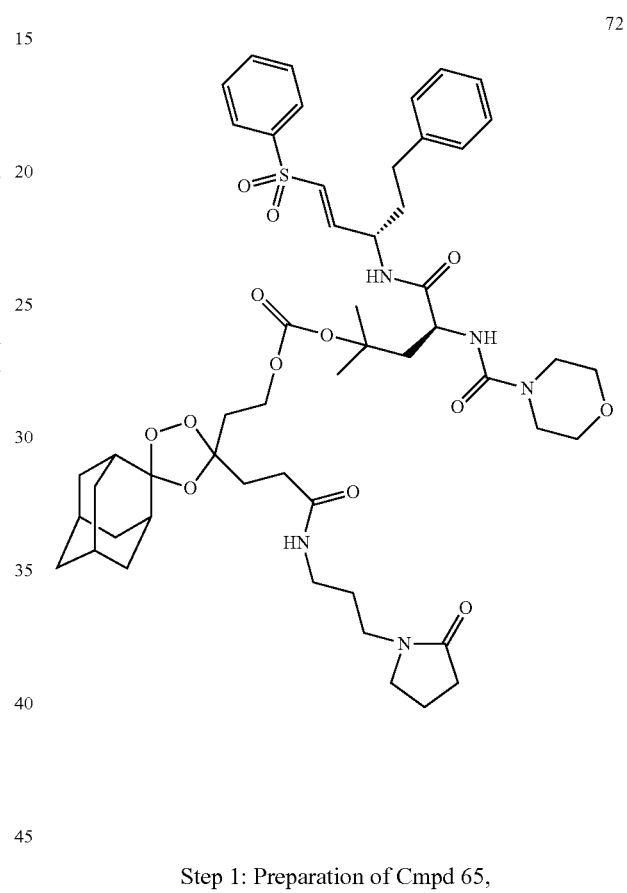

72

Step 1: Preparation of Cmpd 65, (S)-2-amino-4-methylpentane-1,4-diol

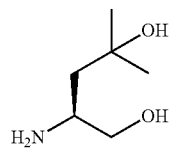

65

A mixture of (4S)-4-(2-hydroxy-2-methylpropyl)-1,3-oxazolidin-2-one (1.0 g, 6.28 mmol), barium hydroxide (3.2 g, 18.8 mmol), ethanol (50 mL) and water (50 mL) was heated to reflux for 4 hours. See Gauthier et al., 2008, *Bioorg. Med. Chem. Lett.*, 18:923-928. After cooling, dry ice (5.5 g, 125.6 mmol) was added and the mixture was stirred vigorously overnight. The suspension was then filtered over CELITE®, rinsing with ethanol. The filtrate was diluted with toluene and evaporated to dryness, yielding crude (S)-2-amino-4-methylpentane-1,4-diol (0.7 g) which was used without further purification in the next step.

Step 2: Preparation of Cmpd 66, (S)—N-(1,4-dihydroxy-4-methylpentan-2-yl) morpholine-4-carboxamide

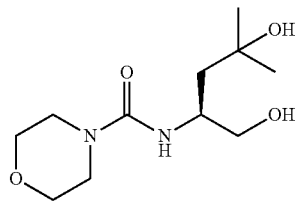

(S)-2-amino-4-methylpentane-1,4-diol (0.6 g, 4.5 mmol) was dissolved in anhydrous dichloromethane (10 mL) and the solution was cooled to 0° C. Next, 4-morpholinecarbonyl chloride (0.78 mL, 6.75 mmol) was added, followed by triethylamine (0.75 mL, 5.4 mmol). The reaction was stirred for 3 hrs at 0-5° C. The solvent was evaporated and the residue was purified using silica gel chromatography (10% methanol-dichloromethane) to afford Cmpd 66. Yield: 0.675 g (61%). MS (m/z): (M+H)=247.

Step 3: Preparation of Cmpd 67, (S)—N-(1-(tert-butyldimethylsilyloxy)-4-hydroxy-4-methylpentan-2-yl) morpholine-4-carboxamide

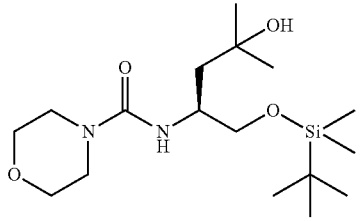

(S)—N-(1,4-dihydroxy-4-methylpentan-2-yl) morpholine-4-carboxamide (0.2 g, 0.809 mmol) was dissolved in anhydrous dimethylformamide (2 mL), and the solution was cooled to −10° C. tert-Butyldimethylsilyl chloride (0.12 g, 0.809 mmol) was added to the reaction followed by imidazole (80 mg, 1.218 mmol), and the resulting solution was stirred for 3 hrs at −10° C. The reaction mixture was poured into saturated sodium bicarbonate solution (50 mL). The aqueous layer was extracted with dichloromethane (100 mL). The organic layer was then washed with 0.3 N cold HCl, (25 mL), dried (Na₂SO₄), filtered and evaporated to afford Cmpd 67 as a white solid. Yield: 0.157 g (55%).

Step 4: Preparation of Cmpd 68, (S)-5-(tert-butyldimethylsilyloxy)-2-methyl-4-(morpholine-4-carboxamido)pentan-2-yl-4-nitrophenyl carbonate

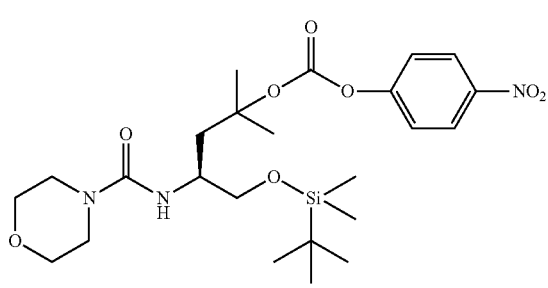

(S)—N-(1,4-dihydroxy-4-methylpentan-2-yl) morpholine-4-carboxamide (90 mg, 0.25 mmol) was dissolved in anhydrous dichloromethane (1 mL). Pyridine (0.03 mL, 0.375 mmol) was added and the reaction was stirred for 5 min. 4-nitrophenyl chloroformate (0.151 g, 0.75 mmol) was then dissolved in anhydrous dichloromethane (0.75 mL) and added to the reaction mixture dropwise. The reaction was stirred under argon for 4-5 h. The reaction mixture was then diluted with dichloromethane (5 mL) and washed with saturated sodium bicarbonate solution (10 mL). The organic layer was then dried (Na₂SO₄), filtered and evaporated to afford a yellowish white solid. The solid was purified further using silica gel chromatography (50% ethyl acetate-hexanes) to afford Cmpd 68. Yield: 90 mg (70%). MS (m/z): (M+H)=527.

Step 5: Preparation of Cmpd 69

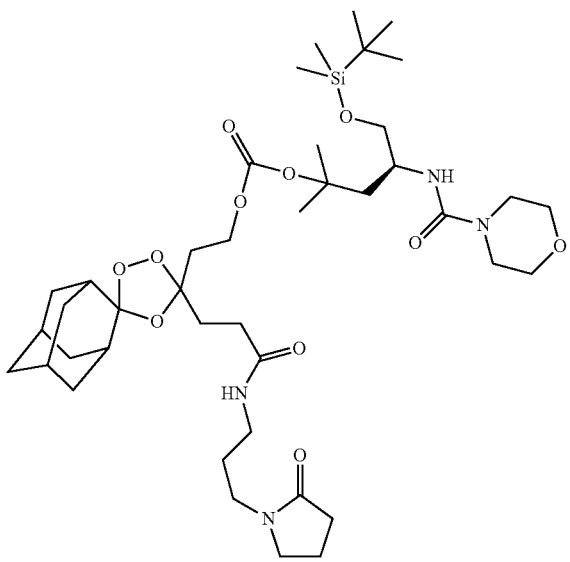

(S)-5-(tert-butyldimethylsilyloxy)-2-methyl-4-(morpholine-4-carboxamido) pentan-2-yl-4-nitrophenyl carbonate (60 mg, 0.114 mmol) and 3-(3-(2-hydroxyethyl)-5,5-spiroadamantyl-1,2,4-trioxolan-3-yl)-N-(3-(2-oxopyrrolidin-1-yl)propyl)propanamide (25 mg, 0.057 mmol) were mixed together in toluene (1 mL). 4-dimethylaminopyridine (30 mg, 0.228 mmol) was then added and the reaction was stirred at 55° C. for 24 h. The solvent was evaporated and the residue obtained was dissolved in dichloromethane (5 mL). The organic solution was washed with saturated sodium bicarbonate (10 mL), dried (Na₂SO₄) and evaporated to afford a yellowish solid. The solid was purified using silica gel chromatography (5% methanol-dichloromethane) to afford Cmpd 69. Yield: 32 mg (35%). MS (m/z): (M+H)=823.

Step 6: Preparation of Cmpd 70

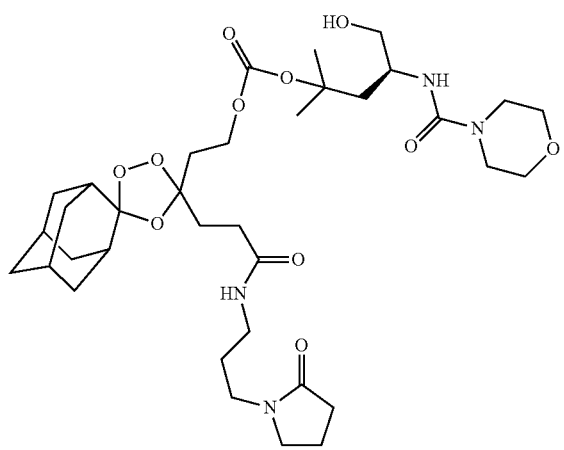

A solution of Cmpd 69 (30 mg, 0.036 mmol) in tetrahydrofuran was treated with tetrabutyl ammonium fluoride (0.08 mL of 1.0 M solution in tetrahydrofuran) and stirred for 2 h at 0° C. The solvent was evaporated and the residue was dissolved in dichloromethane (2 mL). The organic solution was washed with saturated ammonium chloride (2 mL), dried ($Na_2SO_4$), filtered and evaporated. The Cmpd 79 obtained was used without further purification in the next step.

Step 7: Preparation of Carboxylic acid Cmpd 71

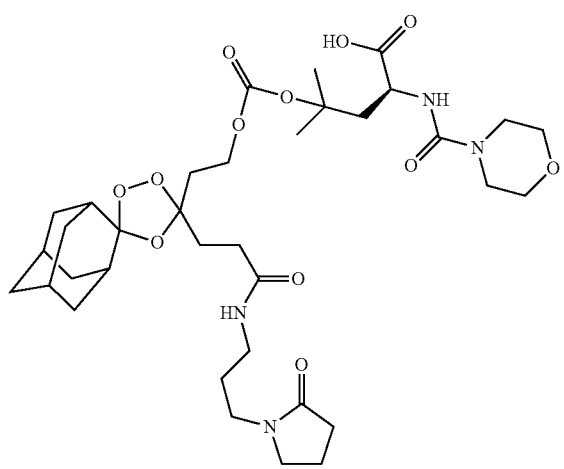

A solution of Cmpd 70 (30 mg, 0.042 mmol) in dichloromethane (1 mL) was treated with the Dess-Martin periodinane (36 mg, 0.084 mmol). The reaction mixture was stirred for 2 hr after which it was diluted with diethyl ether and dichloromethane (1 mL). This was followed by addition of 2 mL 1:1 mixture of saturated sodium bicarbonate and sodium thiosulphate. The biphasic mixture was allowed to stir until the two phases become clear. The aqueous layer was separated and washed with ether (1 mL). The organic layers were combined, dried ($Na_2SO_4$), filtered and evaporated to afford the crude aldehyde. The aldehyde was dissolved in a mixture of tert-butanol-water (5:1, 1 mL), and the reaction mixture cooled to 0° C. Next, a solution of 2.0 M isobutylene in THF (excess, 0.1 mL) was added, followed by $Na_2HPO_4$ (18 mg, 0.126 mmol) and $NaClO_2$ (12 mg, 0.126 mmol). The reaction mixture was stirred for 3 hrs 0° C. The solvent was evaporated and the residue was dissolved in dichloromethane. The organic layer was washed with saturated ammonium chloride, dried ($Na_2SO_4$), filtered and evaporated to afford the acid Cmpd 71, which was used without further purification in the next step. Yield: 15 mg (50%). MS (m/z): (M+H)=723.

Step 8: Preparation of Cmpd 72

A mixture of carboxylic acid Cmpd 71 (10 mg, 0.014 mmol) and (S)-3-benzenesulfonyl-1-phenethylallylamine tosylate (8 mg, 0.016 mmol) was taken into dimethylformamide (0.5 mL). See Somoza et al. *Biochemistry*, 2000, 39(41): 12543-51. The reaction mixture was treated with diisopropylethylamine (7.2 µl, 0.414 mmol) and 2-(7-Aza-1H-benzotriazole-1-yl)-1,1,3,3-tetramethyluronium hexafluorophosphate (8 mg, 0.020 mmol) and stirred for 2 hours under argon. Saturated aqueous sodium bicarbonate was then added to the reaction mixture. The resulting solution was then extracted with dichloromethane. The organic layers were combined, washed with saturated sodium chloride, dried ($Na_2SO_4$), filtered, and concentrated to afford the crude compound. This material was purified by preparative HPLC (0.05% TFA: methanol: $H_2O$) to afford Cmpd 72. Yield: 5 mg (36%). MS (m/z): (M+H)=1006.

Example 14

Evaluation of Drug Release in Cells

Cmpd 72 is the prodrug form of a parasite cysteine protease inhibitor, specifically an inhibitor of the proteases falcipain-2 and falcipain-3 from the malaria parasite *Plasmodium falciparum*. Inhibition of these proteases in cultured *P. falciparum* parasites is known to produce a distinctive phenotype—a swollen, dark-staining food vacuole (Rosenthal, et al: *J Clin Invest*, 1988, 82:1560). Without wishing to be bound by any theory, it is believed that the prodrug form of the protease inhibitor (e.g., Cmpd 72) does not itself inhibit falcipain-2 or falcipain-3 due to the substantial pro-moiety present in the prodrug form. Thus, observation of the food vacuole phenotype upon treatment of cultured *P. falciparum* parasites with the protease inhibitor prodrug would constitute positive evidence for release of the free drug inside the parasite.

Figure 3A:
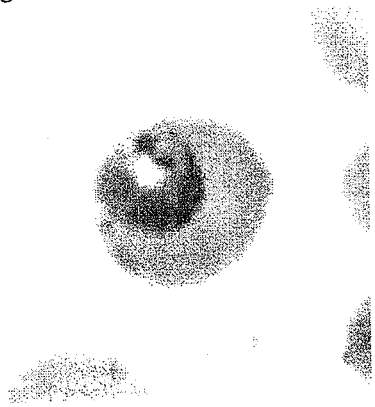
FIG. 3. Photomicrographs of W2 strain *P. falciparum* parasites grown as described herein and incubated in the presence of test and control compounds for 24 hrs. A): DMSO; B) Compound E64 (as described herein) at 3.3 uM; C) drug moiety of Cmpd 72 at 1.1 uM (N—((S)-4-hydroxy-4-methyl-1-oxo-1-((S,E)-5-phenyl-1-(phenylsulfonyl)pent-1-en-3-ylamino)pentan-2-yl)morpholine-4-carboxamide); D) Cmpd 58 at 1.1 uM; E) Cmpd 72 at 1.1 uM.
Figure 3B:
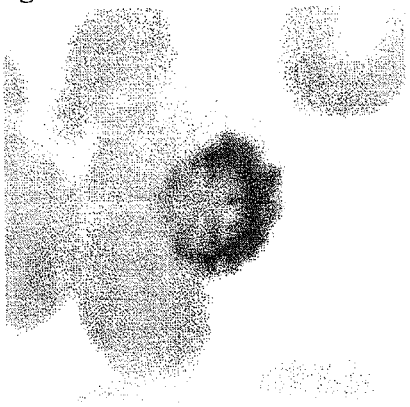
Figure 3C:
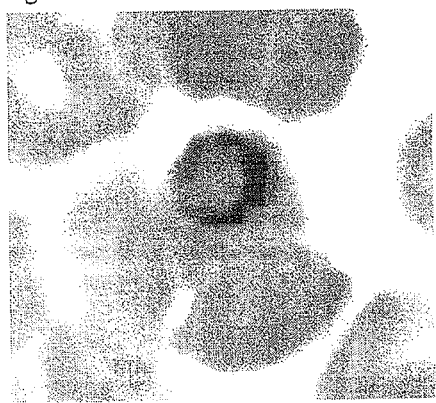
Figure 3D:
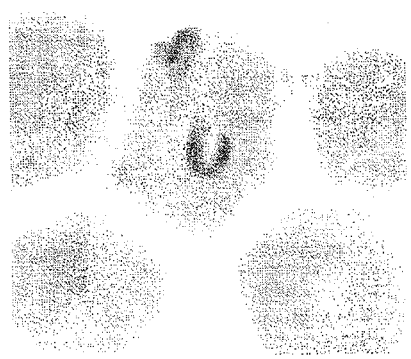
Figure 3E:
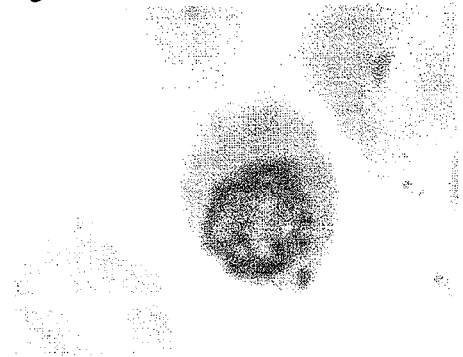

Synchronized W2 strain *P. falciparum* parasites (ring stage) were grown as described herein and incubated in the presence of test and control compounds for 24 hrs. Next, a blood smear was made, fixed with methanol, and stained with Giemsa, as known in the art. Parasites were then imaged at 100× magnification to identify the presence or absence of the food vacuole phenotype. As shown in FIG. 3A, untreated control parasites (DMSO) show a normal, light-staining food vacuole. In contrast, parasites treated with the protease inhibitor control E64 (FIG. 3B) show a swollen, dark-staining food vacuole, consistent with falcipain inhibition. Similarly, parasites treated with the protease inhibitor (drug moiety) present in Cmpd 72 also show a swollen, dark-staining food vacuole. See FIG. 3C. Treatment of parasites with the pro-moiety alone (Cmpd 58, Example 10) does not produce the protease-inhibited phenotype, as expected. See FIG. 3D. Finally, treatment of parasites with the prodrug Cmpd 72 does produce the falcipain-inhibited phenotype, consistent with successful release of the active protease inhibitor from the prodrug form.

Example 15

Demonstration of Fe$^{II}$ Activation and Drug Release In Vitro

In a series of experiments, the compound of Example 1 (0.03 mM) was incubated with various amounts (0-100 equivalents) of a ferrous iron salt (ferrous bromide) in a 1:1 solution of acetonitrile and an aqueous buffer at ambient temperature. Either of two buffers were used in these studies: pH 5.5 sodium acetate buffer intended to mimic a lysosomal environment or pH 7.4 phosphate buffered saline. At various time points, a 10 µl sample of the incubation mixture was removed and analyzed by liquid chromatography/mass spectroscopy (LC/MS) to identify the expected products of iron-promoted degradation and drug release. A Waters Alliance/ZQ micromass LC/MS system and a 15 min method employing gradient elution with acetonitrile-water mobile phase (containing 0.1% formic acid) was employed. In the absence of ferrous iron salts, the compound of example 1 was stable for 48 hrs, showing no detectable chemical degradation by LC/MS spectroscopy. In the presence of ferrous bromide however, the compound of example 1 was rapidly (less than 1 hour) converted into the expected ketone (analogous to G, FIG. 2) resulting from iron-promoted degradation of the trioxolane ring. Also observed was a signal attributable to the released drug species, 2,5-dichloroaniline. During the course of the experiment, the quantity of 2,5-dichloroaniline increased, which is consistent with the desired retro-Michael reaction (beta-elimination) releasing drug species.

Example 16

Evaluation of Antimalarial Activity

Cultures of 3D7 and W2 strains of *P. falciparum* parasites were grown in purified human erythrocytes and synchronous cultures were placed into 96-well plates containing test compounds. After a 72 hr growth period, cultures were fixed for 1 hr at room temperature in 1% paraformaldehyde and stained with 50 nM YOYO-1 for about 24 hr in the dark. Samples were analyzed on a Becton-Dickinson LSR2 fitted with a microplate reader. Uninfected erythrocytes were used to determine background autofluorescence. Parasite growth in each sample was determined relative to infected erythrocytes without test compound. "Eight-point dose-response curves were generated and EC$_{50}$ values determined using GRAPH-PAD PRISM® software". The EC$_{50}$ values (nM) for the compounds of examples 1, 2, 4, and 5 are provided in Table 1.

TABLE 1

Antimalarial activity (EC$_{50}$ in nM) of selected compounds described herein against 3D7 and W2 strains of *P. falciparum*.

| Structure | Compound (Example) | EC50 (nM) 3D7 strain | W2 strain |
|---|---|---|---|
| 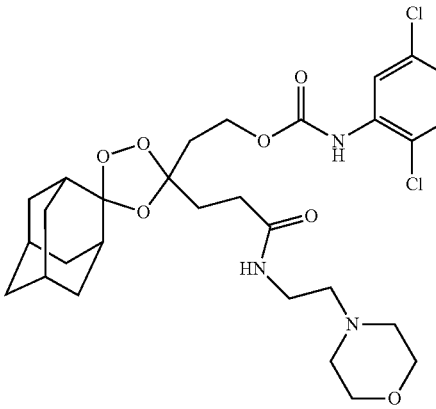 | 40 (1) | 16 | 24 |
| 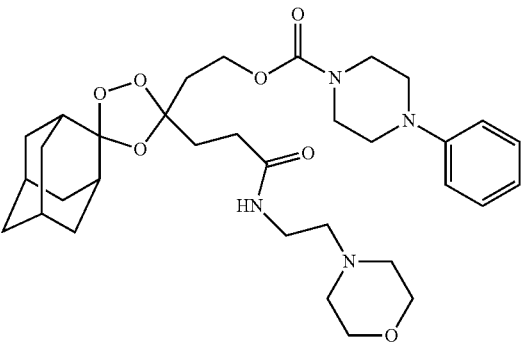 [SMILES: O=C(CCC1(CCOC(=O)N2CCN(c3ccccc3)CC2)OOC2(O1)C1CC3CC(C1)CC2C3)NCCN1CCOCC1] | 45 (2) | 9.0 | 4.9 |

TABLE 1-continued

Antimalarial activity (EC$_{50}$ in nM) of selected compounds described herein against 3D7 and W2 strains of *P. falciparum*.

| Structure | Compound (Example) | EC50 (nM) 3D7 strain | W2 strain |
|---|---|---|---|
| 46 | 46 (3) | | |
| 47 | 47 (4) | 16 | 15 |
| 48 | 48 (5) | 38 | 62 |

TABLE 1-continued

Antimalarial activity (EC$_{50}$ in nM) of selected compounds described herein against 3D7 and W2 strains of *P. falciparum*.

| Structure | Compound (Example) | EC50 (nM) 3D7 strain | W2 strain |
|---|---|---|---|
| 49 | 49 (6) | | |
| 51 | 51 (7) | | |
| 53 | 53 (8) | | |

TABLE 1-continued

Antimalarial activity ($EC_{50}$ in nM) of selected compounds described herein against 3D7 and W2 strains of *P. falciparum*.

| Structure | Compound (Example) | EC50 (nM) 3D7 strain | W2 strain |
|---|---|---|---|
| 57 | 57 (9) | | |
| 61 | 61 (11) | | |
| 64 | 64 (12) | | |

TABLE 1-continued

Antimalarial activity (EC$_{50}$ in nM) of selected compounds described herein against 3D7 and W2 strains of *P. falciparum*.

| Structure | Compound (Example) | EC50 (nM) 3D7 strain | W2 strain |
|---|---|---|---|
| | 72 (13) | | |

72

Example 17

Fluorescence Microscopy Studies

In order to further study the fate of fragmenting compounds as described herein within cultured parasites, fluorescence microscopy studies can be conducted. For example, the 4-nitrobenzo-2-oxa-1,3,-diazole (NBD) fluorophore has been used previously in studies of artemisinin (Stocks et al., 2007, *Angewandte Chemie International Edition*, 46(33):6278-6283.) and remains fluorescent over a wide pH range, including the acidic pH (~5) of the *P. falciparum* food vacuole. Microscopes, and techniques thereof, most relevant to the experiments to be conducted include an inverted epifluorescence microscope optimized for time lapse imaging, and a spinning disk confocal microscope. Both microscopes can be equipped with temperature-, humidity-, and $CO_2$-controlled incubators, and both have been used successfully for imaging *P. falciparum*-infected erythrocytes. The epifluorescence microscope can have, for example, a hardware autofocus system (Nikon Perfect Focus) and be optimized for long-term time lapse imaging. The confocal microscope can be optimized, for example, for high detection sensitivity, with a back-thinned EMCCD camera (Photometrics Cascade II) which can be useful for observing the more subtle effects of biological action of compounds on cultured parasites. Additional studies can involve combinations of compounds as described herein and iron chelating reagents. The fluorescence, or lack thereof, of *P. falciparum*-infected cells pre-treated with iron chelating reagents prior to contact with fluorophoric compounds described herein can demonstrate the specific role of iron in the scission of the prodrug.

Example 18

Evaluations of Morphologies of Malaria Parasites

Fragmentation of compounds described herein within parasites can be detected by observation of characteristic morphological changes produced by the antimalarial component of the compound released within the parasite. The success of this approach would require that 1) the intact prodrug does not itself possess the secondary activity, and 2) the drug, once released and free of the prodrug, can produce an interpretable morphology even in the presence of trioxolane-derived activity. Exemplary morphological change include, but are not limited to, swollen food vacuoles, which are indicative of inhibition of falcipains, and multiple vesicles within the food vacuole. These class-specific morphological effects can be exploited to observe prodrug fragmentation in cultured parasites. The results can be confirmed by testing such prodrugs in a biochemical assay. In further investigations, synchronized parasite cultures can be incubated with test prodrugs as described herein for different intervals during different portions of the 48 hour *P. falciparum* life cycle. At various time points thin smears can be prepared, fixed with methanol, and stained with Giemsa, as known in the art. Visualization of fixed smears can be accomplished with a bright field microscope with oil immersion lens (100×). Morphologies can be compared with those of control parasites incubated with equal concentrations of vehicle, for example DMSO (usually 0.1%, which has no obvious impact on cultured parasites) and with artemisinin, chloroquine, and other drugs known in the art. The observation of a falcipain-inhibited morphology in such experiments can provide evidence for prodrug fragmentation. Finally, the use of iron chelating reagents like deferipone (DFP) can be used to block trioxolane activation, thereby providing an additional control that can greatly aid in the interpretation of experimental results. Thus, successful fragmentation of prodrug is expected to produce a food vacuole morphology in cultured parasites. However, this morphology should not be observed in the case of prior treatment with an iron chelator, since trioxolane activation and subsequent fragmentation would be blocked.

Example 19

Availability of Parasites with Varied Sensitivity to Aminoquinolines and Cystein Protease Inhibitors For proof-of-concept for treatment using compounds described herein, studies can be conducted to evaluate the relative sensitivity to compounds and components thereof of parasites with known sensitivities to antimalarial drugs. For example, parasites with varied sensitivity to trioxolanes can be evaluated as they become available. Furthermore, for aminoquinolines, the sensitivities of available isolates to chloroquine, amodiaquine, piperaquine, and others varies widely, and has been catalogued for many strains. A large number of characterized strains are available for example from the Malaria Reagent Repository (MR4) including culture-adapted strains from Uganda, an area with high-level aminoquinoline resistance, which have recently become available.

What is claimed is:
1. A prodrug having the formula

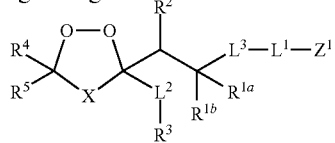

wherein,
X is —O—;
$Z^1$ together with $L^1$ is a drug;
$L^1$ is —N($R^6$)—, —O— or —OC(O)—;
$L^2$ is a bond, substituted or unsubstituted alkylene, substituted or unsubstituted heteroalkylene, —C(O)N($R^7$)— or —N($R^7$)—C(O)—;
$L^3$ is —OC(O)— or a bond, with the proviso that if $L^1$ is —OC(O)—, then $L^3$ is a bond;
$R^{1a}$ and $R^{1b}$ are independently hydrogen, substituted or unsubstituted alkyl, substituted or unsubstituted aryl, or substituted or unsubstituted heteroaryl;
$R^2$ is hydrogen or an electron withdrawing moiety;
$R^3$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^4$ and $R^5$ are joined together to form a ring moiety having at least 6 atoms, said ring moiety selected from substituted or unsubstituted cycloalkyl or substituted or unsubstituted heterocycloalkyl;
$R^6$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and
$R^7$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
wherein said drug is an anti-malarial drug or anti-cancer drug capable of treating malaria or cancer that is associated with a cell or organism having increased $Fe^{II}$ levels compared to $Fe^{II}$ levels in mammalian plasma.

2. The prodrug of claim 1, wherein $R^6$ is hydrogen, unsubstituted alkyl or unsubstituted heteroalkyl.

3. The prodrug of claim 1, wherein $R^6$ is hydrogen or unsubstituted $C_1$-$C_{10}$ alkyl.

4. The prodrug of claim 1, wherein $R^6$ is hydrogen.

5. The prodrug of claim 1, wherein $L^3$ is a bond.

6. The prodrug of claim 1, wherein $L^3$ is —O—C(O)— and $L^1$ is —NH— or —O—.

7. The prodrug of claim 1, wherein $L^1$ is —$NR^6$— and $R^6$ is hydrogen.

8. The prodrug of claim 1, wherein $R^{1a}$, $R^{1b}$, and $R^2$ are hydrogen.

9. The prodrug of claim 1, wherein $R^{1a}$ is methyl or phenyl and $R^2$ is cyano.

10. The prodrug of claim 1, wherein $R^{1a}$ is phenyl and $R^2$ is cyano.

11. The prodrug of claim 1, wherein $R^{1a}$ is phenyl and $R^2$ is H.

12. The prodrug of claim 1, wherein $L^2$ has the formula —$(CH_2)_w$—C(O)NH—$(CH_2)_z$— or —$(CH_2)_w$—NHC(O)—$(CH_2)_z$—, and $R^3$ is substituted or unsubstituted heterocycloalkyl, or substituted or unsubstituted heteroaryl, wherein w and z are independently integers from 0 to 20.

13. The prodrug of claim 12, wherein $R^3$ is morpholino, and w and z are independently integers from 1 to 5.

14. The prodrug of claim 1, wherein $R^4$ and $R^5$ are joined together to form a substituted or unsubstituted adamantyl, or substituted or unsubstituted cyclohexyl.

15. The prodrug of claim 1, wherein $R^4$ and $R^5$ are joined together to form a substituted or unsubstituted adamantyl.

16. The prodrug of claim 1, wherein the drug is an anti-cancer drug.

17. The prodrug of claim 1, wherein the drug is an anti-malarial drug.

18. A method of treating a mammalian disease that is associated with a cell or organism having increased $Fe^{II}$ levels compared to $Fe^{II}$ levels in mammalian plasma, said method comprising administering an effective amount of a compound to a patient in need of such treatment, said compound being the prodrug of claim 1.

* * * * *